Figure 2:
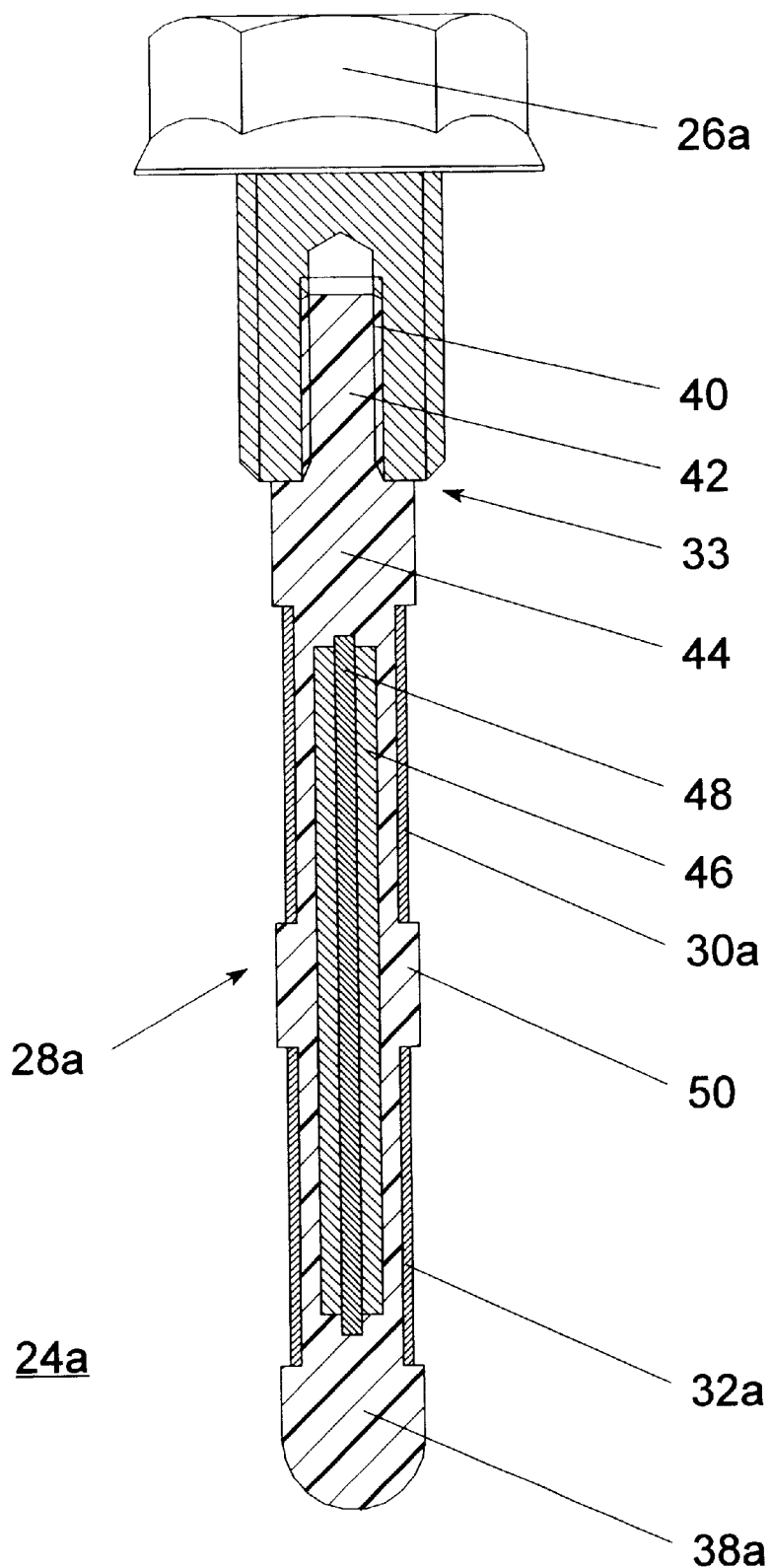

United States Patent [19]
Rehberg et al.

[11] Patent Number: 6,034,295
[45] Date of Patent: Mar. 7, 2000

[54] IMPLANTABLE DEVICE HAVING AN INTERNAL ELECTRODE FOR STIMULATING GROWTH OF TISSUE

[75] Inventors: Christoph Rehberg, Bauer st. 31, Munich, Germany; Werner Kraus, Munich, Germany

[73] Assignee: Christoph Rehberg, Munich, Germany

[21] Appl. No.: 08/753,895

[22] Filed: Dec. 2, 1996

[30] Foreign Application Priority Data

Nov. 30, 1995 [DE] Germany .......................... 195 44 750

[51] Int. Cl.[7] ................ A61F 2/28; A61F 2/32; A61F 2/36; A61N 1/08
[52] U.S. Cl. .................... 623/16; 623/1; 623/8; 623/11; 623/12; 623/18; 623/20; 623/22; 623/23; 607/51; 607/116; 607/137; 433/201.1; 606/62; 606/67
[58] Field of Search ................ 623/1, 8, 11, 12, 623/16, 17, 18, 20, 22, 23; 606/60–69; 433/201.1; 607/50, 51, 116, 137

[56] References Cited

U.S. PATENT DOCUMENTS

| | | | |
|---|---|---|---|
| 3,745,995 | 7/1973 | Kraus | 623/16 X |
| 3,820,534 | 6/1974 | Kraus et al. . | |
| 3,915,151 | 10/1975 | Kraus | 607/51 X |
| 3,918,440 | 11/1975 | Kraus | 607/51 X |
| 3,964,473 | 6/1976 | Wickham et al. | 623/23 |
| 4,027,392 | 6/1977 | Sawyer et al. | 433/201.1 X |
| 4,052,754 | 10/1977 | Homsy | 623/16 X |
| 4,195,367 | 4/1980 | Kraus | 623/22 X |
| 4,214,322 | 7/1980 | Kraus | 623/22 X |
| 4,216,548 | 8/1980 | Kraus | 623/22 X |
| 4,781,591 | 11/1988 | Allen . | |
| 5,030,236 | 7/1991 | Dean | 623/18 X |
| 5,651,767 | 7/1997 | Schulman et al. | 623/12 X |

FOREIGN PATENT DOCUMENTS

| | | |
|---|---|---|
| 2 315 517 | 10/1973 | Germany . |
| 26 11 744 | 9/1977 | Germany . |
| 26 11 744 C2 | 9/1977 | Germany . |
| 30 03 758 A1 | 8/1981 | Germany . |
| 30 03 758 C2 | 8/1981 | Germany . |
| 34 14 992 A1 | 10/1985 | Germany . |
| 1 400 680 | 7/1975 | United Kingdom . |

OTHER PUBLICATIONS

Kraus, W.: "Therapie des Knochens und des Knorpels, mit schwacher, langsam–schwingender elektromagnetischer Energie" (Therapy of the Bone and Cartilage, with Weak, Low–Frequency Electromagnetic Enery), in: Medizinisch–Orthopädische Technik, vol. 98, 1978, Issue 2, pp. 33–43.
"Orthopaedic Product News", May/Jun. 1995, p. 8.
"Osteologie", vol. 5, Issue 2, 1996.

*Primary Examiner*—Mary Beth Jones
*Attorney, Agent, or Firm*—Frishauf, Holtz, Goodman, Langer & Chick, P.C.

[57] ABSTRACT

Implantable device, such as a femoral head prosthesis, with a body (12) of biocompatible material shaped to suit its medical function, which forms an internal cavity (16) and has open apertures (18) that lead from the cavity (16) to the outside. The cavity (16) serves to receive spongiosa or other biological material into which the tissue that surrounds the implanted device is intended to grow through the apertures (18). The device is provided with at least two electrodes (30, 32), at least one of which is located in the cavity (16) spaced apart from the inside of the body (12) that forms the cavity (16). The electrodes are provided with an arrangement for supplying a low-frequency alternating voltage, so that by means of the supplied voltage a low-frequency electrical alternating field and a low-frequency alternating current, whereby the tissue growth is promoted, are created inside the cavity (16).

13 Claims, 19 Drawing Sheets

Fig. 1a
PRIOR ART
Fig. 1b
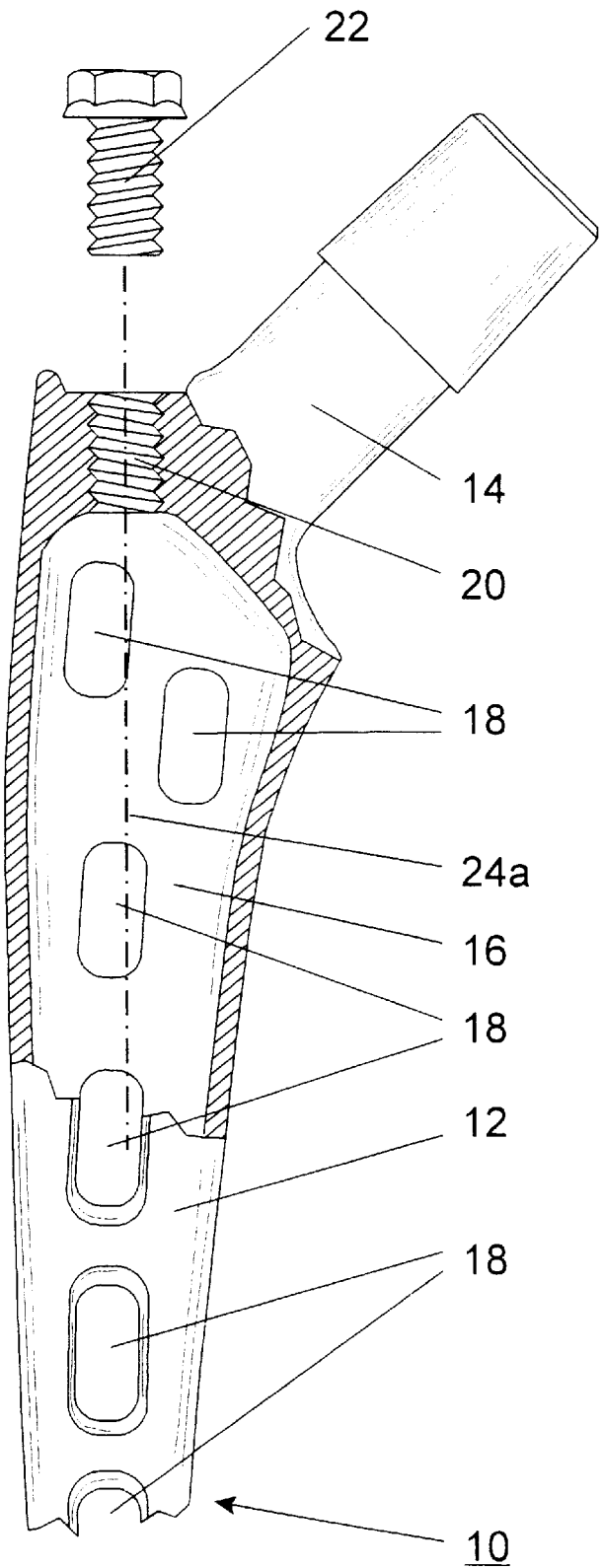
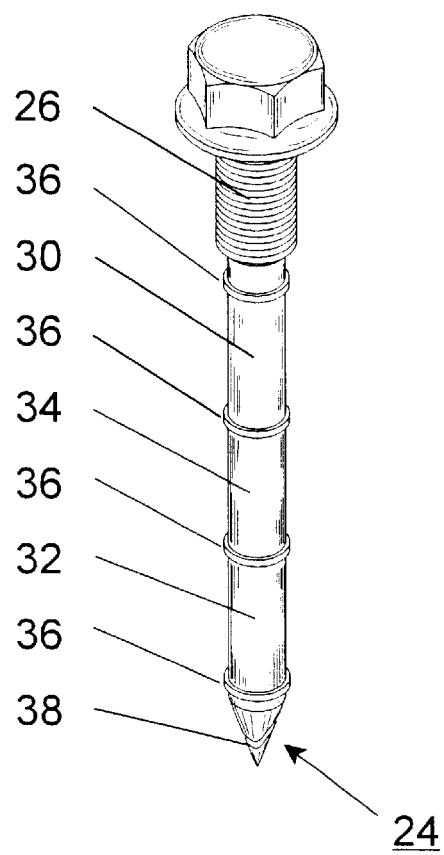

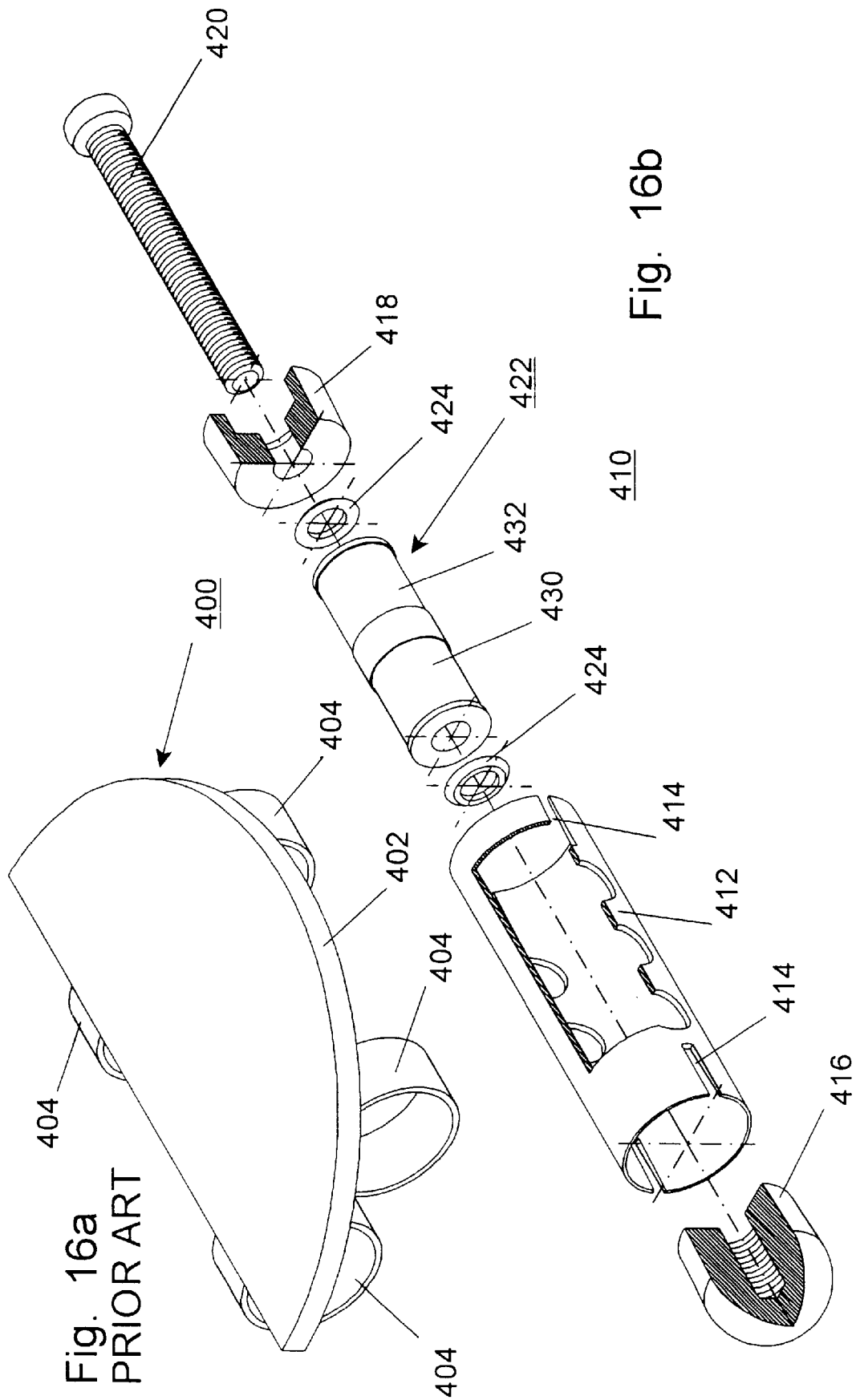

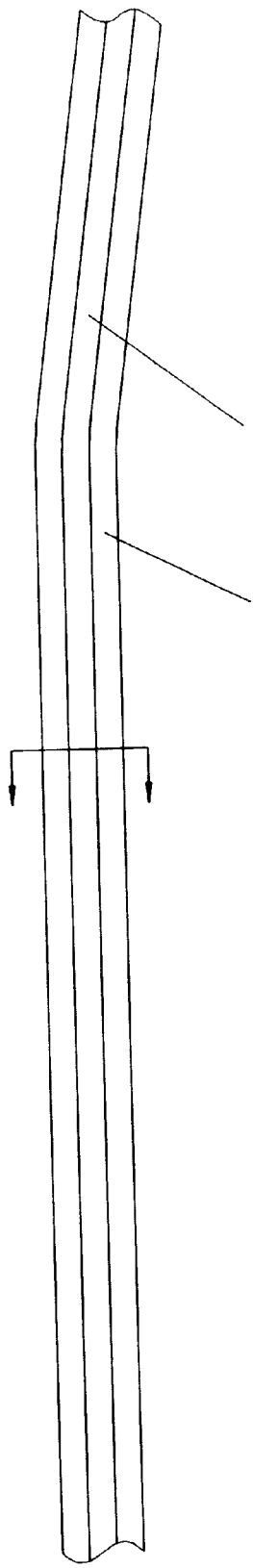
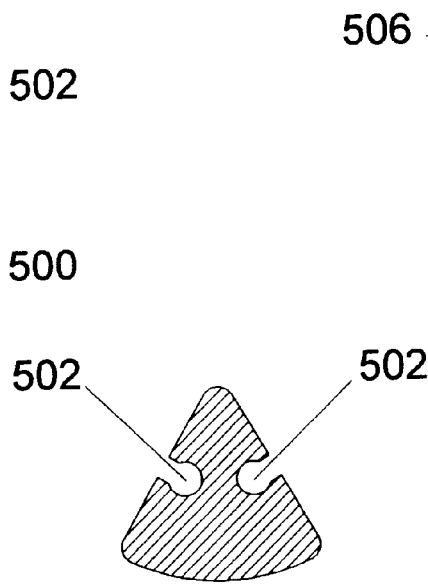
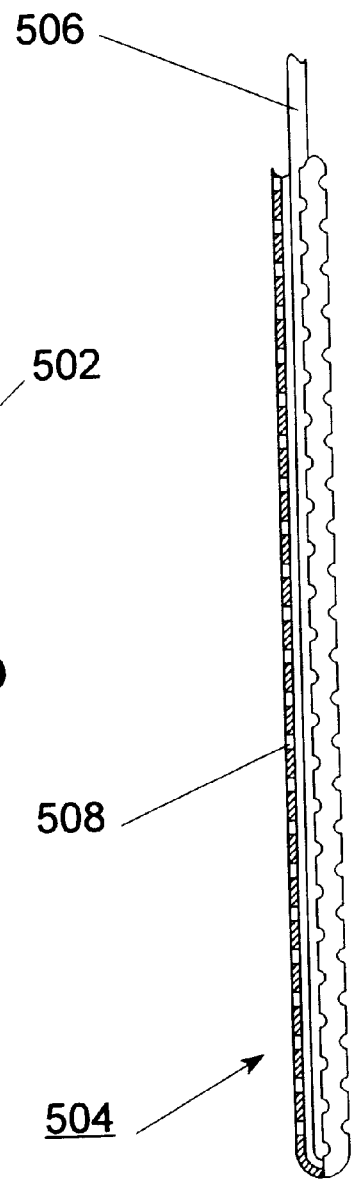
Fig. 17a
Fig. 17b
Fig. 17c

IMPLANTABLE DEVICE HAVING AN INTERNAL ELECTRODE FOR STIMULATING GROWTH OF TISSUE

The present invention relates to an implantable device with a body suitable to its function and comprising biocompatible material; the body forms an inner cavity, has at least one aperture, and is provided with electrodes to which a low-frequency alternating voltage can be supplied.

Devices of the type in question here that can be implanted into the human body, such as joint prostheses, tooth prostheses, cartilage substrates for building up ear tissue, for instance, among others have a load-bearing or form-defining body suitable to its medical function and comprising a biocompatible material, which as metal, plastic or ceramic.

The professional journal OSTEOLOGIE, Vol. 5, No. 2, 1996, p. 87, discloses titanium joint prostheses that are secured to the bone by expanding dowels.

Orthopedic Product News, May/June 1995, page 8, discloses implants for stabilizing backbones.

Implantable devices are also known in which the body forms a cavity and has open apertures that lead to the outside from the cavity. The cavity serves to receive spongiosa or other bioactive material that is intended to promote the growth into the apertures of the tissue surrounding the implanted device. One typical example of such a device is the hip-joint prosthesis developed by Prof. Täger. The femoral head part of this prosthesis has a hollow shaft provided with lateral apertures. The acetabulum part is double-walled and forms an annular cavity. The outer wall forms a kind of male thread and has a series of oblique, slitlike apertures.

It is also known that the growth of human tissue, especially bone tissue, can be promoted by means of a low-frequency alternating current. Devices ("electric implants") that make use of this discovery contain an implantable pickup or secondary coil which is connected or coupled to tissue electrodes, and in which a low-frequency alternating voltage can be induced through an external primary coil. Frequencies below 20 Hz and preferably below 16 or 10 Hz have proven successful; the curve shape should be in the form of sine waves or pulse waves. This principle is also employed in the present invention.

An electric femoral head prosthesis known from German Patent DE-C 23 15 517 has a shaft with a cavity that accommodates a pickup coil. The pickup coil is coupled to electrodes mounted on the outside of the shaft.

An electric tooth prosthesis in the form of a ceramic artificial tooth that contains a pickup coil and has electrodes on its outer surface is known from German Patent DE-C 26 11 744.

A device for maintaining vitality of bone tissue, which has a pickup coil and two electrodes connected to the coil and integrated in a meshlike substrate in the form of a frustoconical jacket, is known from German Patent Disclosure DE-A 30 03 758.

A marrow nail that contains a pickup coil and has two tissue electrodes on its outside is known from U.S. Pat. No. 3,820,534.

From German Patent Disclosure DE-A 34 14 992, an artificial tooth that has a shaft of tissue-compatible metal is known. The shaft has a rectangular diametral aperture on the inner wall of which an electrode is mounted. Between the shaft and the electrode, a low-frequency alternating voltage can be applied in order to promote the growth of the shaft into the jawbone. The current that promotes tissue growth flows essentially from the outer edges of the electrode mounted in the aperture to the edges of the shaft that define the aperture, but do not flow inside the aperture, and thus the tissue is not made to grow into the aperture.

The object of the present invention is to embody an implantable device of the type referred to at the outset such that the growth of the outer tissue into the cavity or cavities of the device is promoted, or in other words a device which has a load-bearing or form-defining body of biocompatible material which is embodied to suit its medical function and forms at least one inner cavity, into which spongiosa or other biologically effective material can be introduced if desired; apertures or openings lead to the outside from the cavity, and the tissue that surrounds the implanted device is intended to grow into the cavity through them.

This object is attained according to the invention in that the device is provided in a known manner with a pickup coil or other current delivering device, which is coupled to at least two electrodes, and that at least one of the electrodes is located inside the cavity in such a way that it is surrounded in spaced-apart fashion by the inner boundary of the cavity.

The region of the cavity between at least one aperture, which in the implanted state of the device is oriented toward the surrounding tissue that is to be made to grow into it, and the electrode located inside the cavity is entirely or partly free of parts of the device, so that it can receive biologically active material and/or ingrowing tissue. If a low-frequency alternating voltage is supplied to the electrodes, a low-frequency electrical alternating field oriented from the inside outward is created and a low-frequency alternating current flows in the interior of the cavity, which promote the growth of the external tissue through the apertures or holes into the cavity and thereby firmly anchor the implant in the surrounding tissue.

The term "apertures" or "holes" as used here means macroscopic holes, not microscopic holes of the type that are typical of fine-pored sintered materials. In rigid implants, the apertures generally have cross-sectional areas in the range from a few to several tens of $mm^2$. In the case of large-pored sintered or meshlike structures, the apertures generally have sizes in the range from a few tenths of one $mm^2$ to a few $mm^2$.

The load-bearing or form-defining body may be shaped extremely variably; for instance, it may have the shape of a femoral head prosthesis, acetabulum prosthesis, or other joint prostheses, or that of an anchor for a tooth prosthesis, a lumbar spine plug or a form-defining meshlike structure onto which an outer ear, nose or the like can be built up.

If the perforated body is electrically conductive and is connected as a counterelectrode to the internal electrode insulated from it inside it, then it may be advantageous to apply a low-frequency alternating voltage between the electrodes, onto which a direct current component is superimposed whose polarity is such that the outer electrode forms the cathode. The magnitude of the direct voltage component can amount for instance to 20% or optionally up to 50% of the usual amplitude of the alternating voltage, the usual amplitude being up to about 700 mV/eff. If an implantable pickup coil is used as the voltage source, then the direct voltage component can be generated by connecting a diode with a resistor parallel to it in the line between one of the electrodes and the associated terminal of the pickup coil.

The invention will be described in further detail below in terms of exemplary embodiments in conjunction with the drawings. Some of the drawing figures are greatly enlarged.

Figure 3:
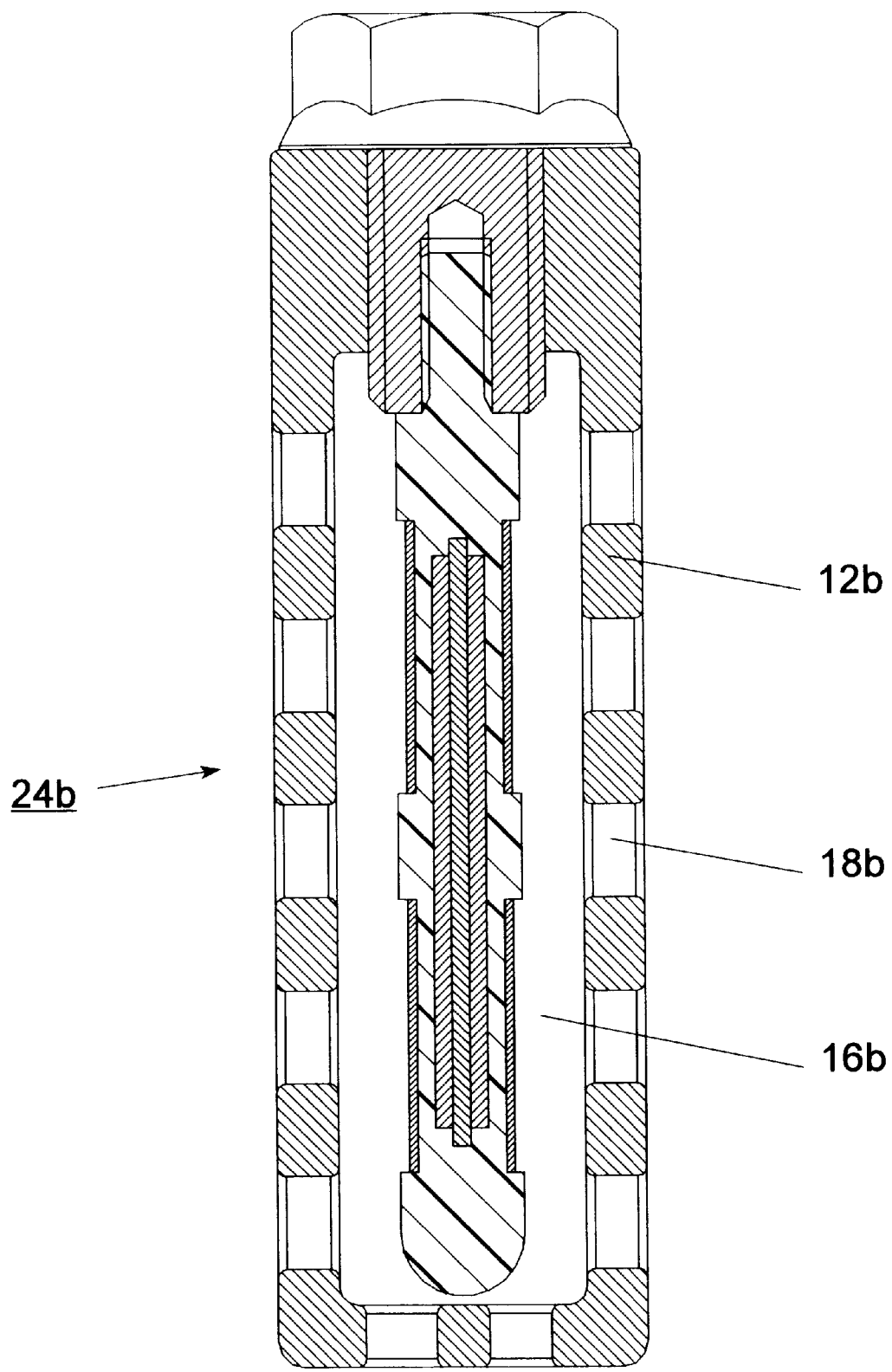
Figure 4A:
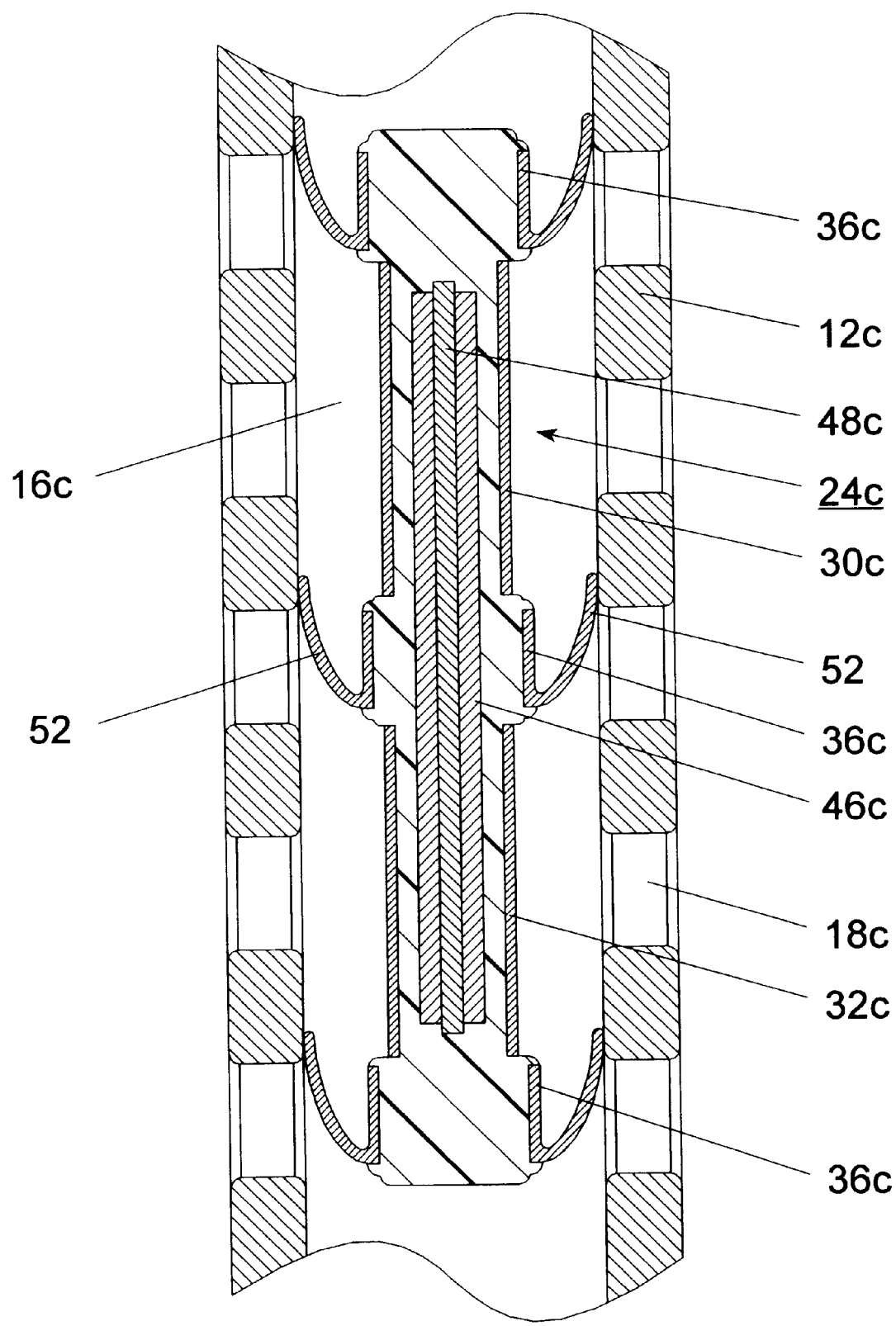
Figure 4B:
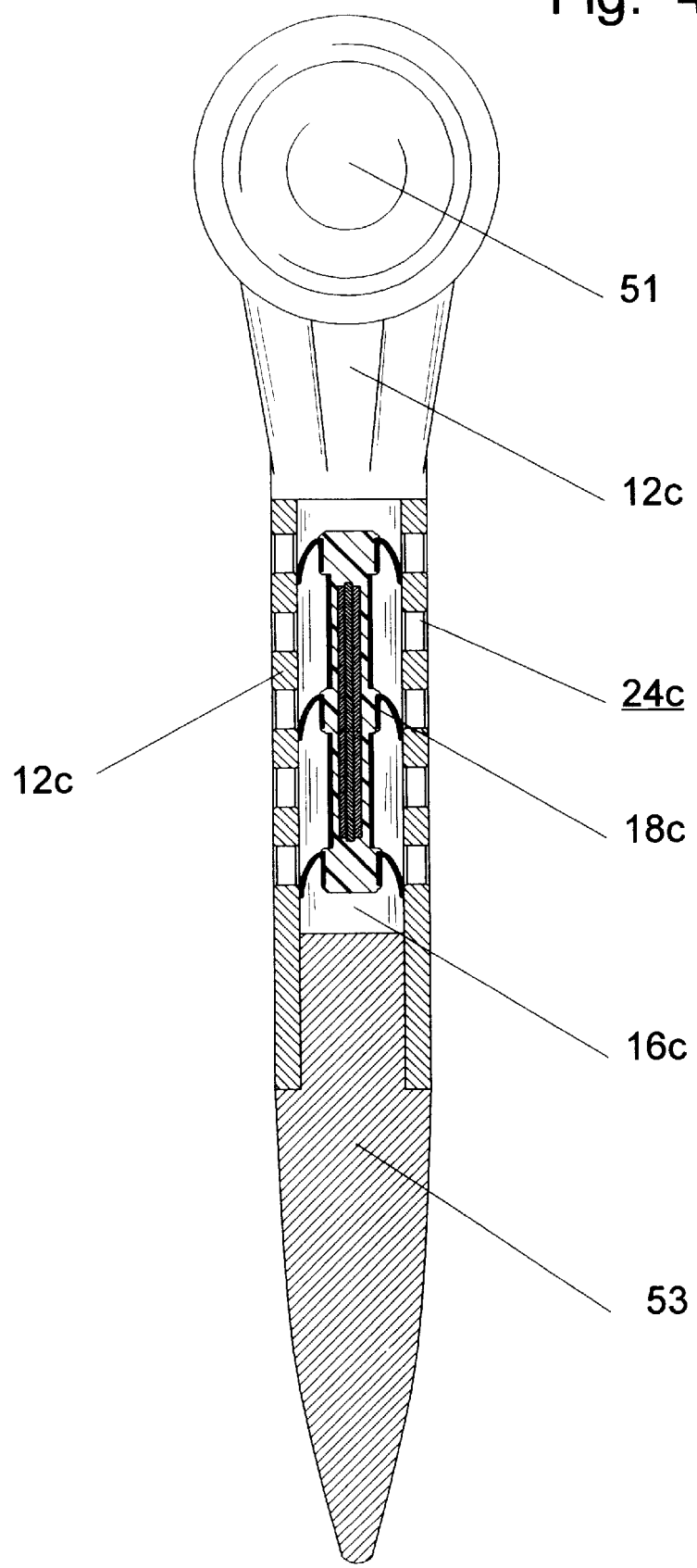
Figure 5:
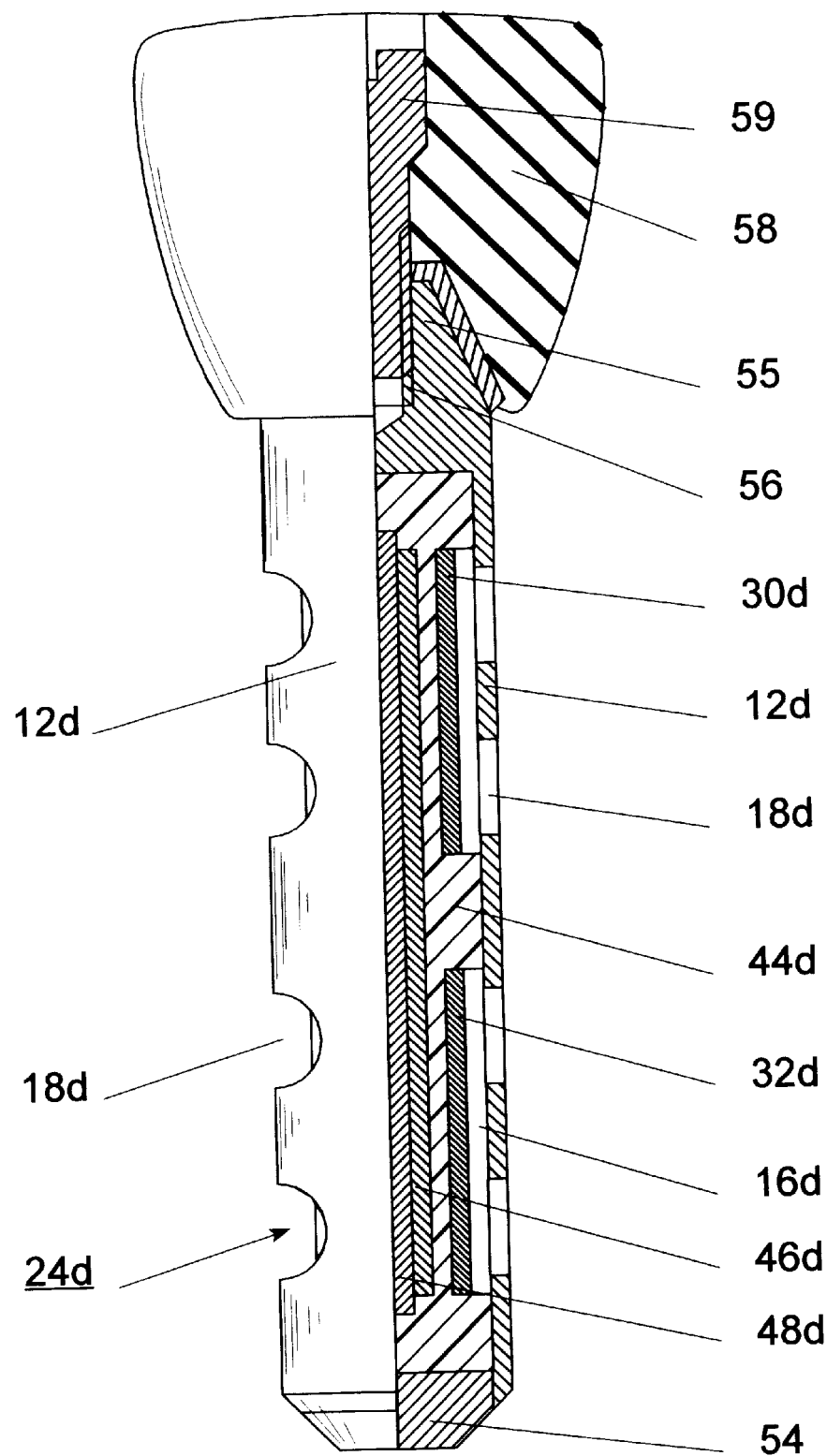
Figure 6:
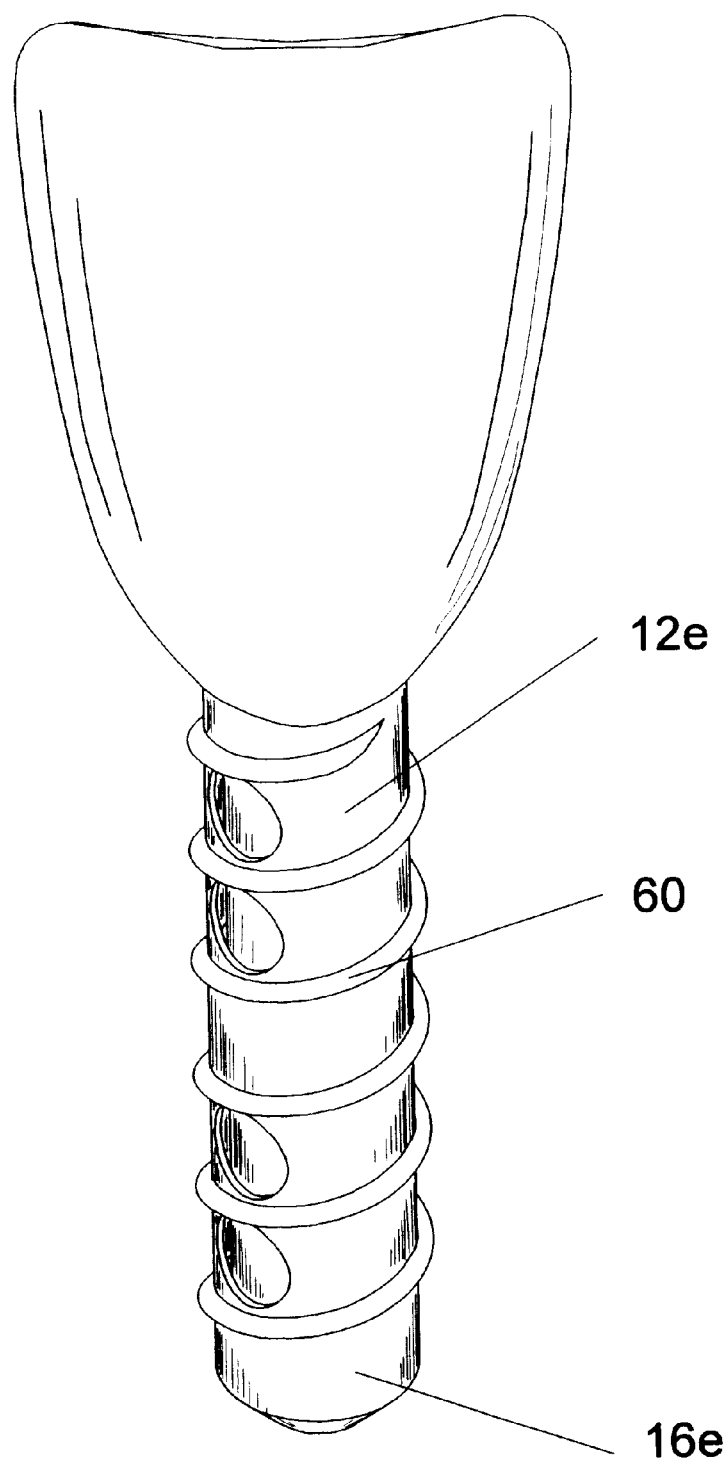
Figure 7A:
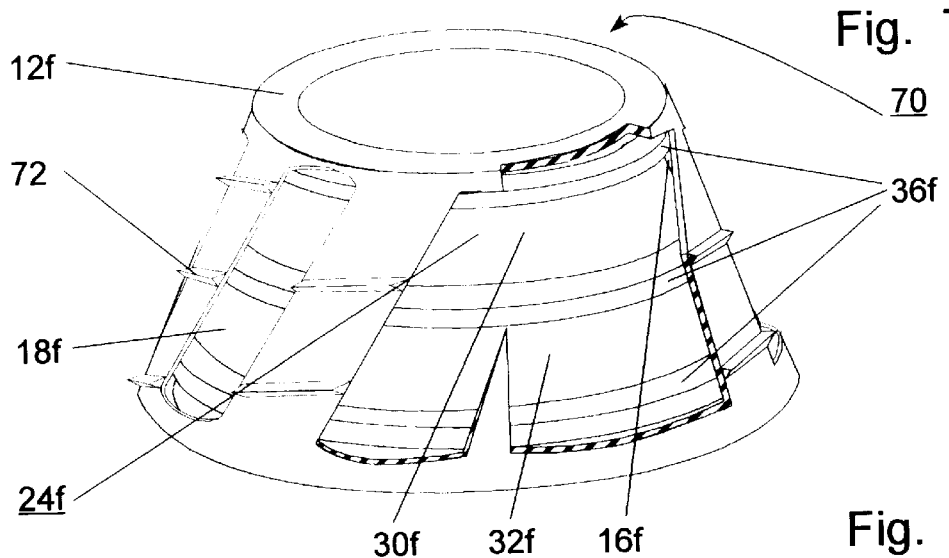
Figure 7B:
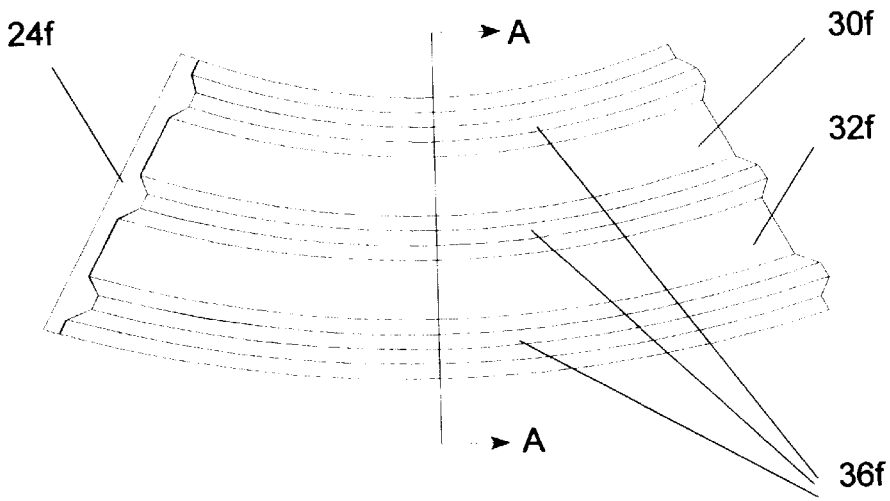
Figure 7C:
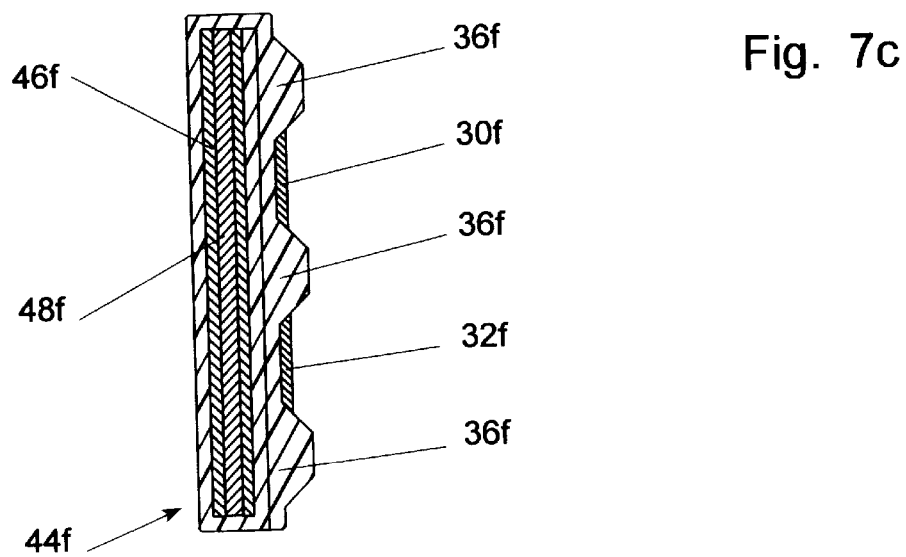
Figure 8A:
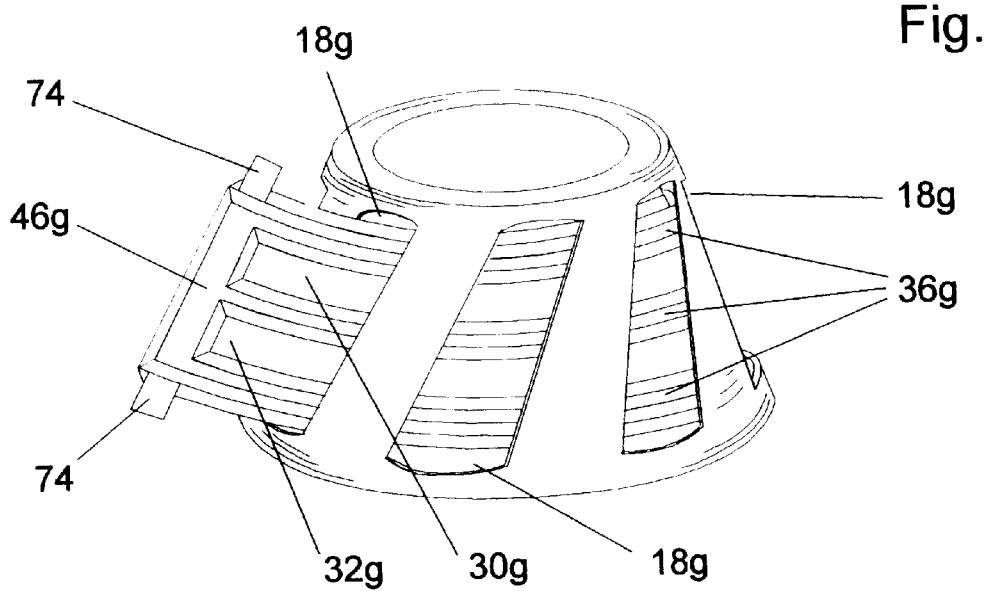
Figure 8B:
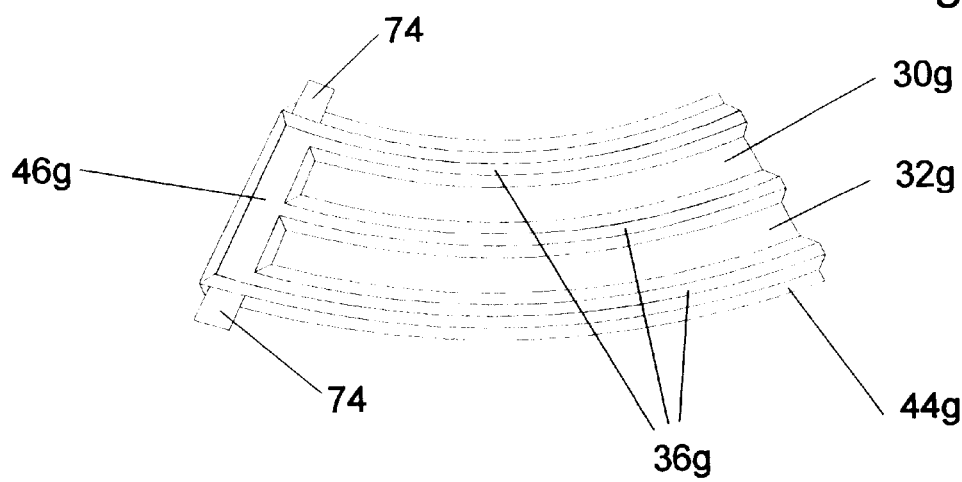
Figure 8C:
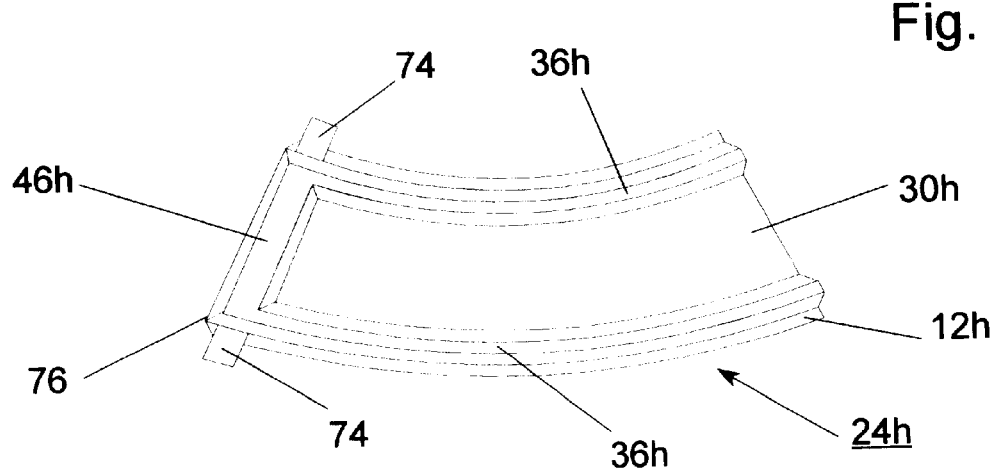
Figure 8D:
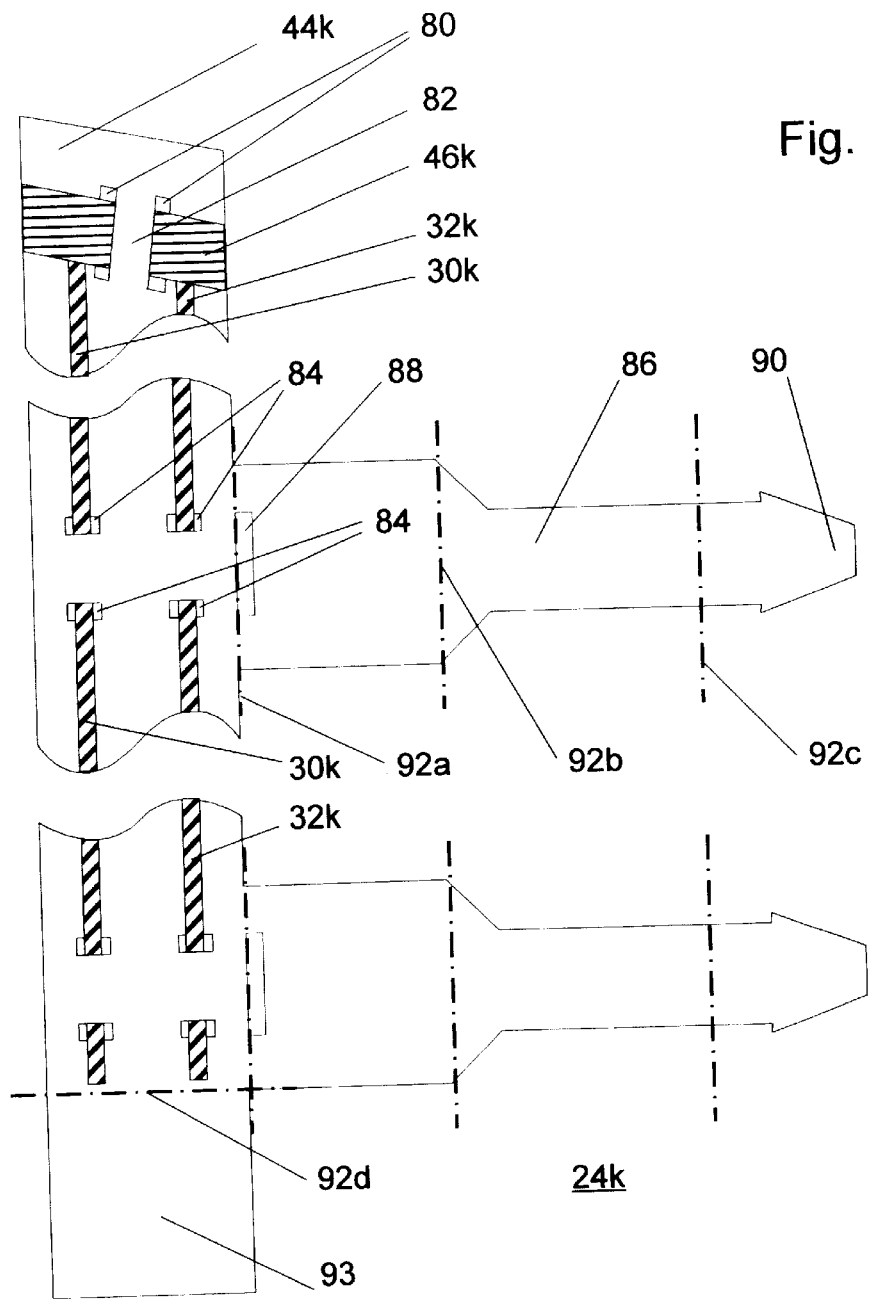
Figure 8E:
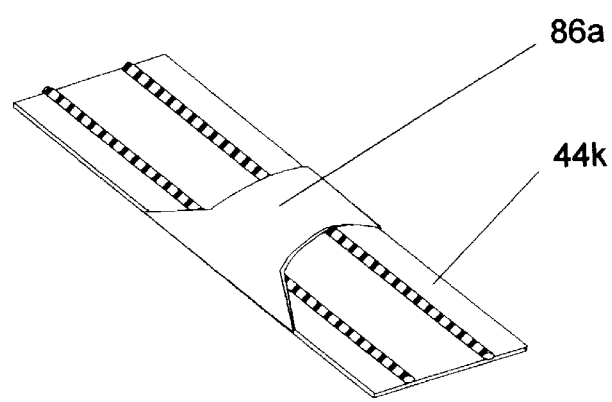
Figure 9A:
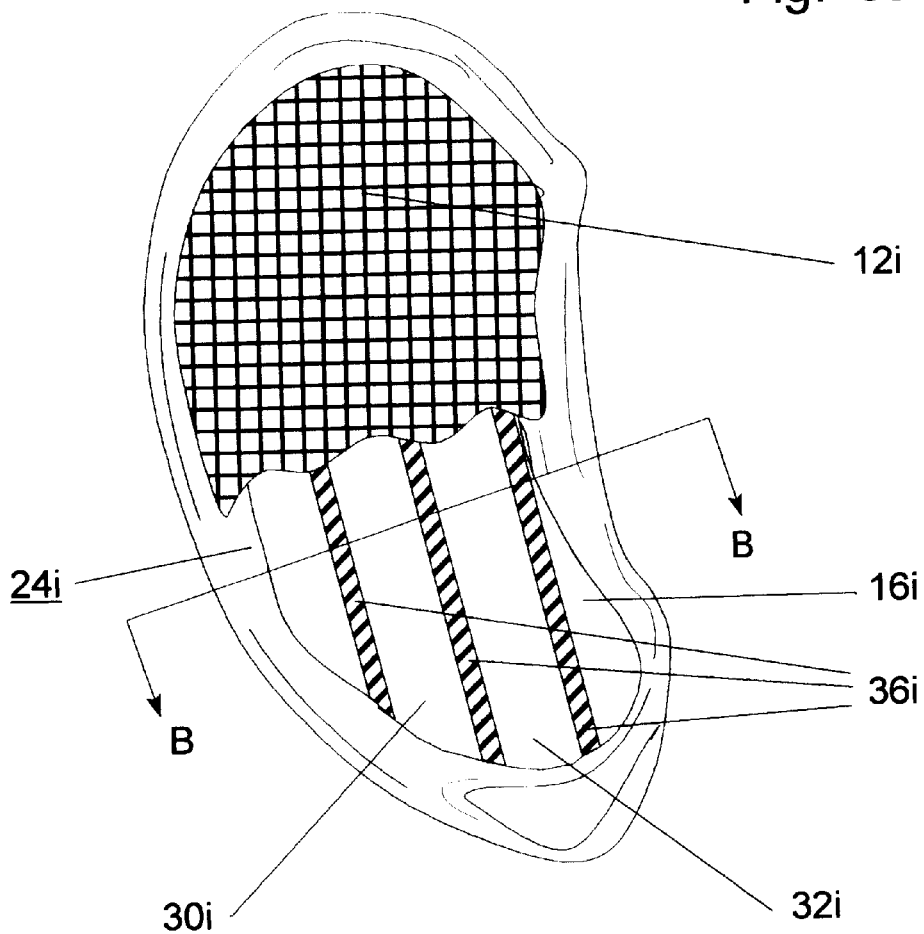
Figure 9B:
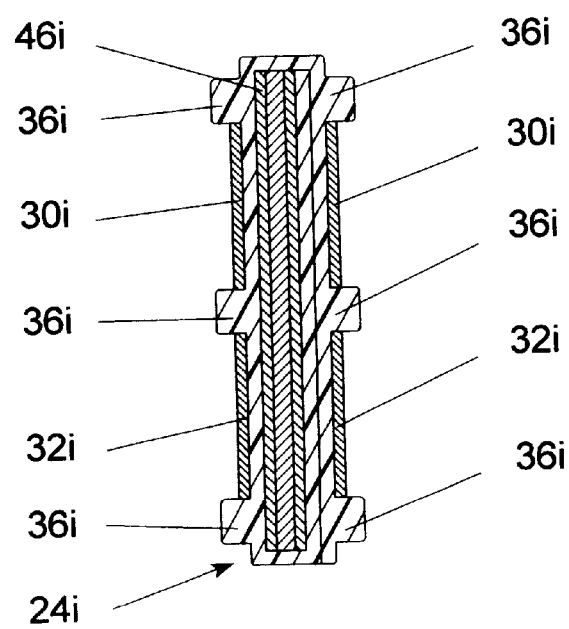
Figure 10:
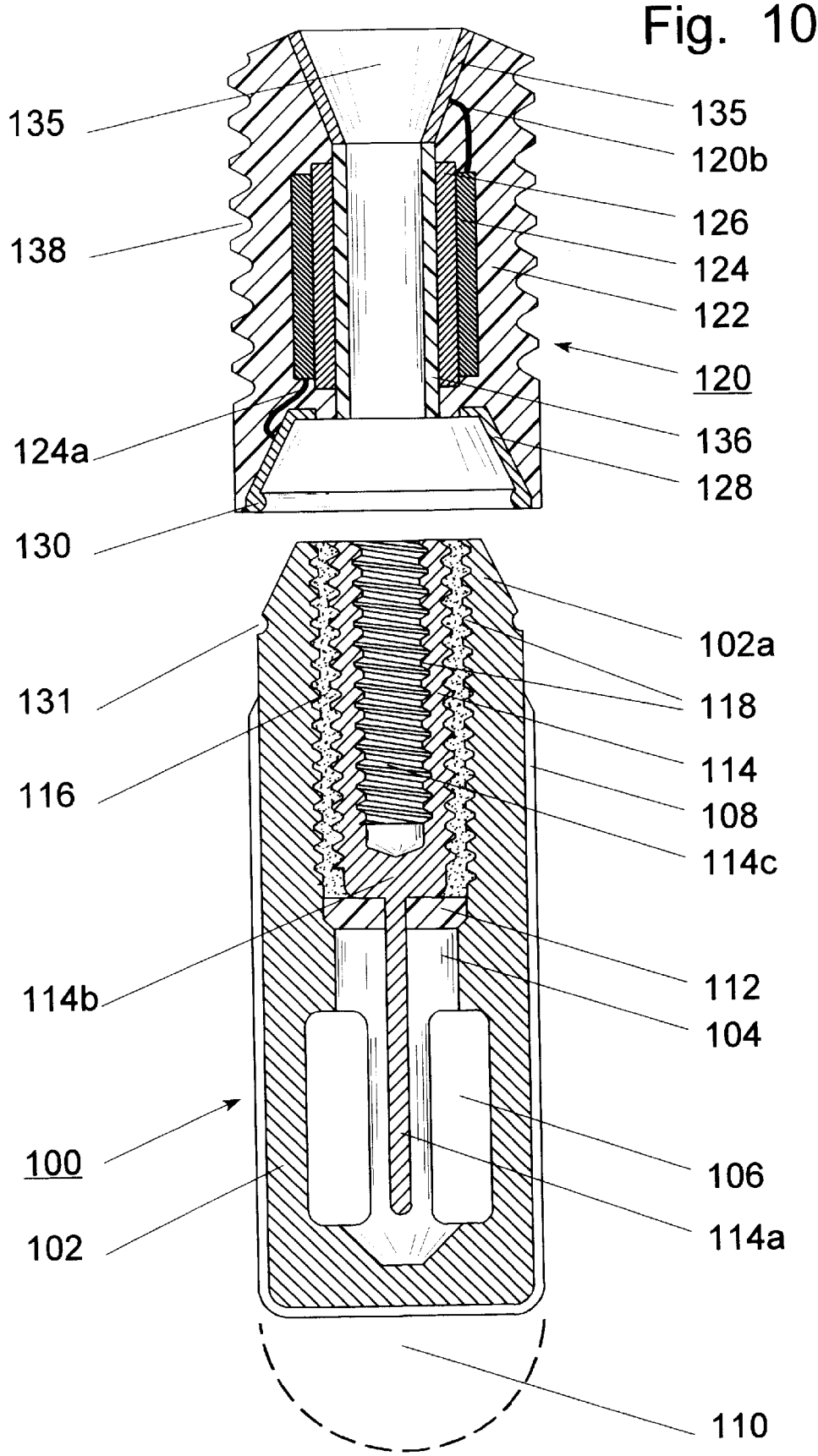
Figure 11:
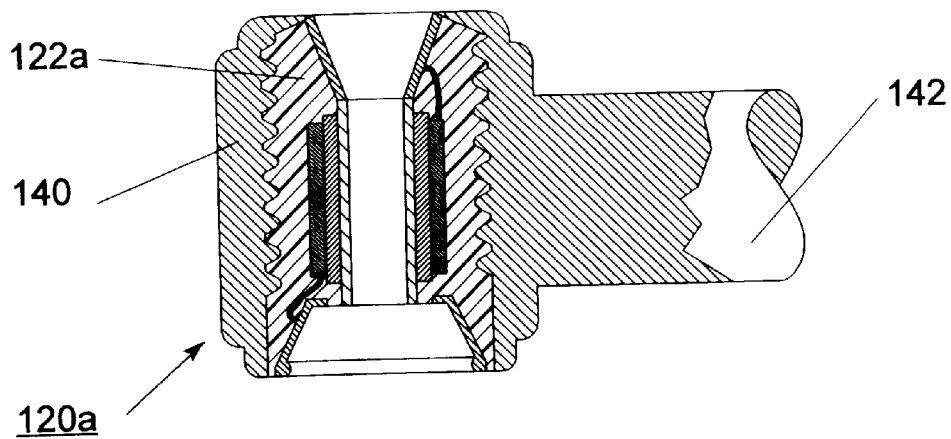
Figure 12:
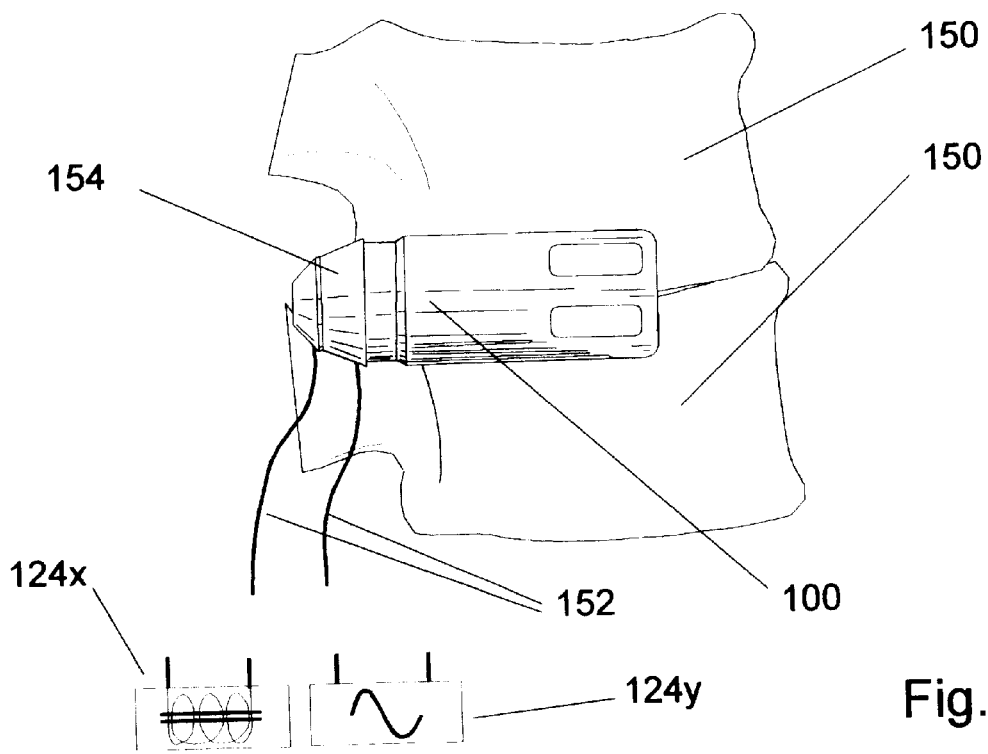
Figure 13:
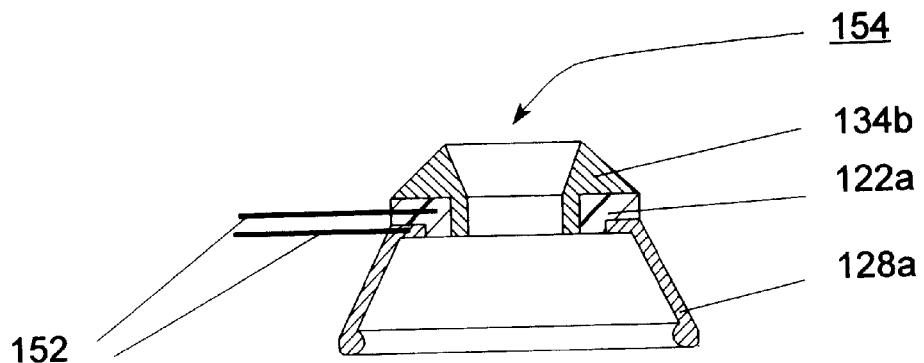
Figure 14A:
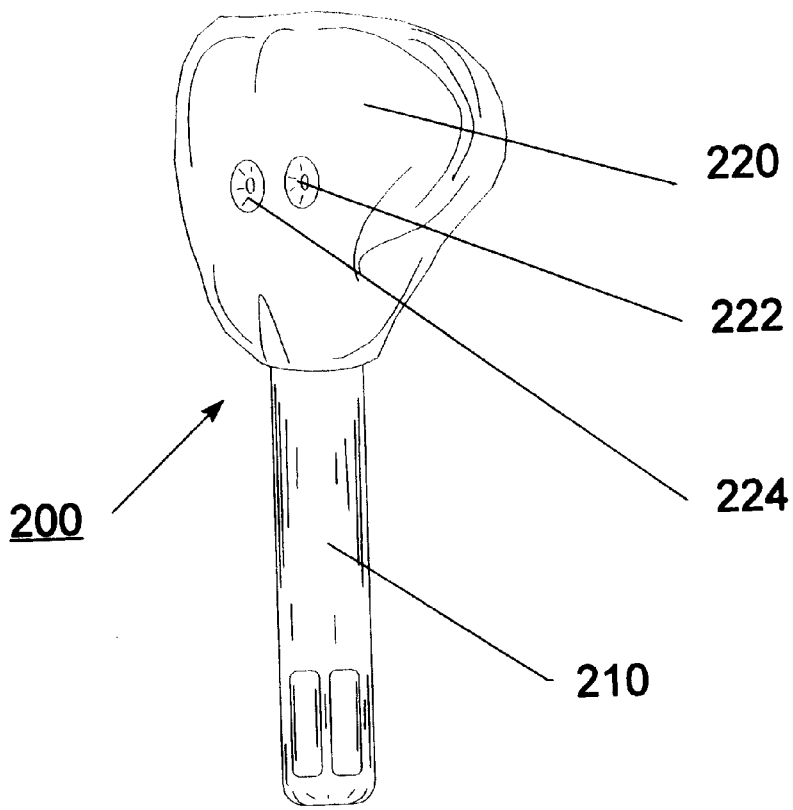
Figure 14B:
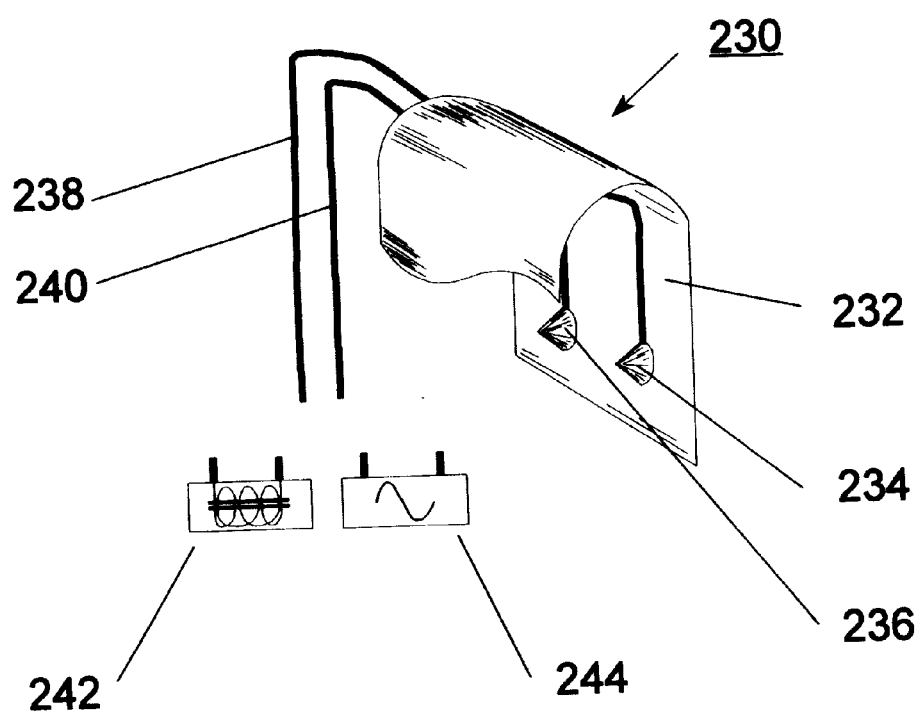
Figure 15:
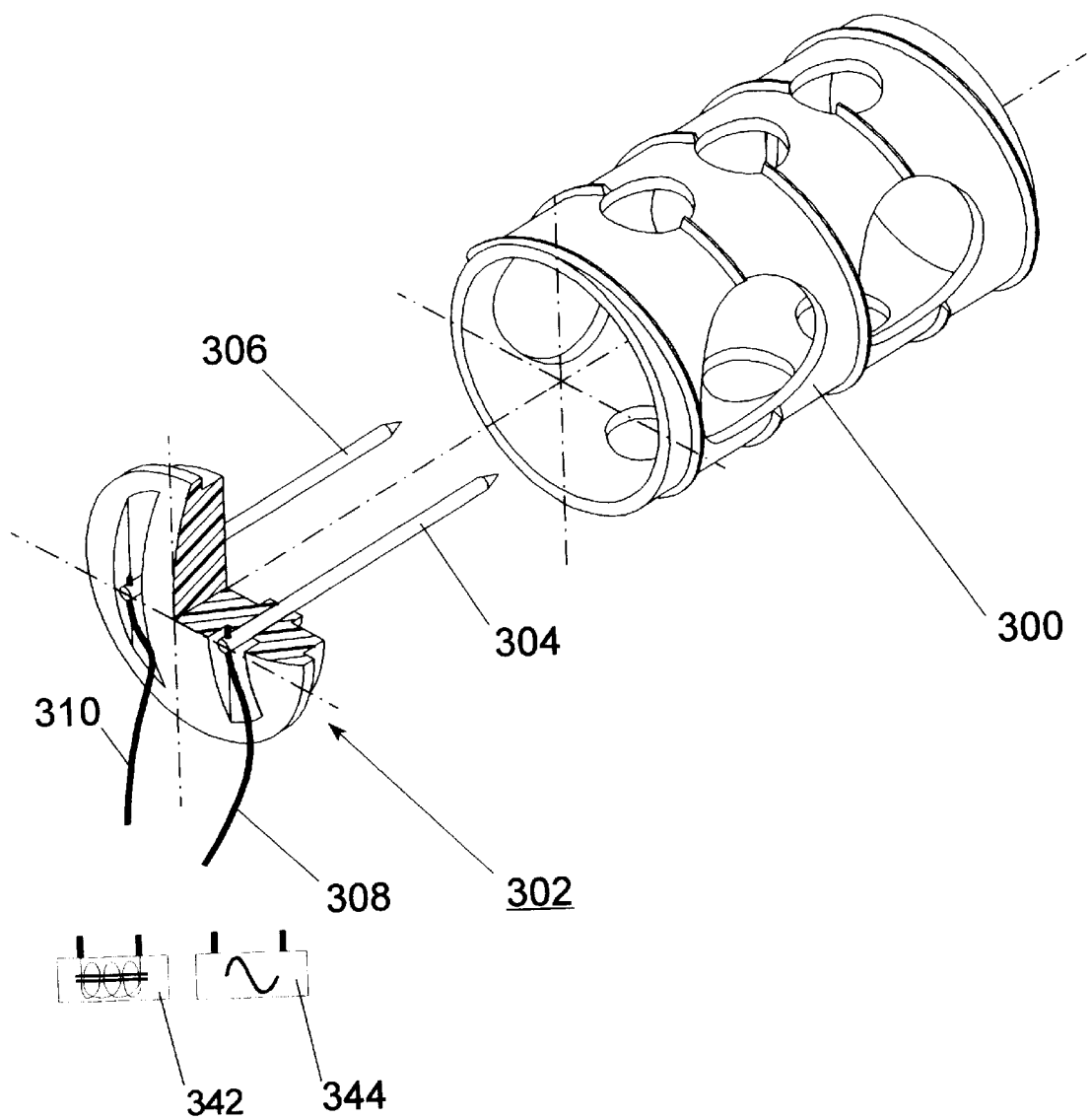

Shown are:

FIG. 1a a sectional view of a known femoral head prosthesis and FIG. 1b an electrifier device or auxiliary device intended for it the device of FIG. 1a;

FIG. 2, a somewhat modified embodiment of the electrifier of FIG. 1b, showing a preferred internal layout of such devices;

FIG. 3, a basic illustration of the further embodiment of the invention;

FIG. 4a, an embodiment of the invention that is especially suitable for a permanently implanted osteosynthesis element;

FIG. 4b, a brachial joint prosthesis corresponding to FIG. 4a;

FIGS. 5 and 6, two exemplary embodiments in the form of dental implants;

FIG. 7a, a perspective view partly in section, of an acetabulum prosthesis according to the invention;

FIG. 7b, a plan view of an electrifier of the prosthesis of FIG. 7a,

FIG. 7c, a somewhat enlarged cross section in the plane A—A of FIG. 7b;

FIG. 8a, a simplified illustration of another embodiment of an acetabulum prosthesis;

FIG. 8b, an illustration of the electrifier of the prosthesis of FIG. 8a;

FIG. 8c, a modification of the electrifier of FIG. 8b;

FIG. 8d, a further modification of the electrifier of FIG. 8b;

FIG. 8e is a fragmentary view of the electrifier of FIG. 8d, with the tab closed;

FIG. 9a, an embodiment that serves to promote the buildup of cartilage and connective tissue;

FIG. 9b, a somewhat enlarged sectional view of the device of FIG. 9a in a plane B—B of FIG. 9a;

FIG. 10, a sectional view of a further dental implant;

FIG. 11, a modified pickup coil unit;

FIG. 12, a device implanted between two lumbar vertebrae;

FIG. 13, a connection cap for the device of FIG. 12;

FIG. 14a, another example of a dental implant;

FIG. 14b, an auxiliary device for coupling an external voltage source to the dental implant of FIG. 14a;

FIG. 15, a further device of the type shown in FIGS. 12 and 13;

FIGS. 16a and 16b, parts of a knee-joint prosthesis;

FIGS. 17a and 17b, a side view and sectional view, respectively, of part of an intramedullary pin;

FIG. 17c, a view partly in section of a device according to the invention for the intramedullary pin of FIGS. 17a and 17b.

Figure 18A:
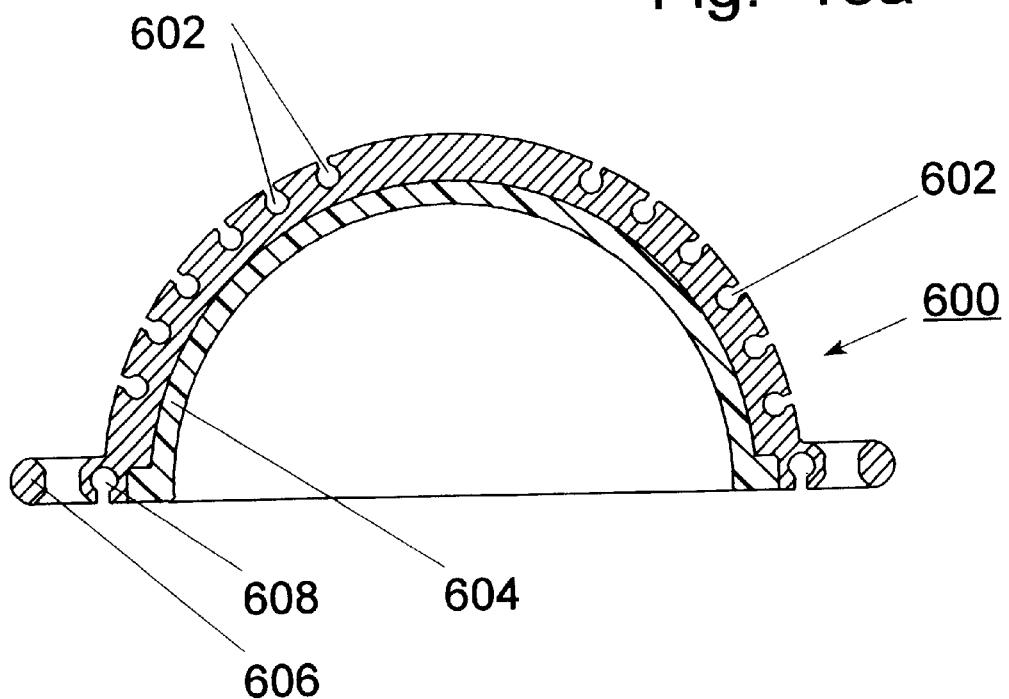
Figure 18B:
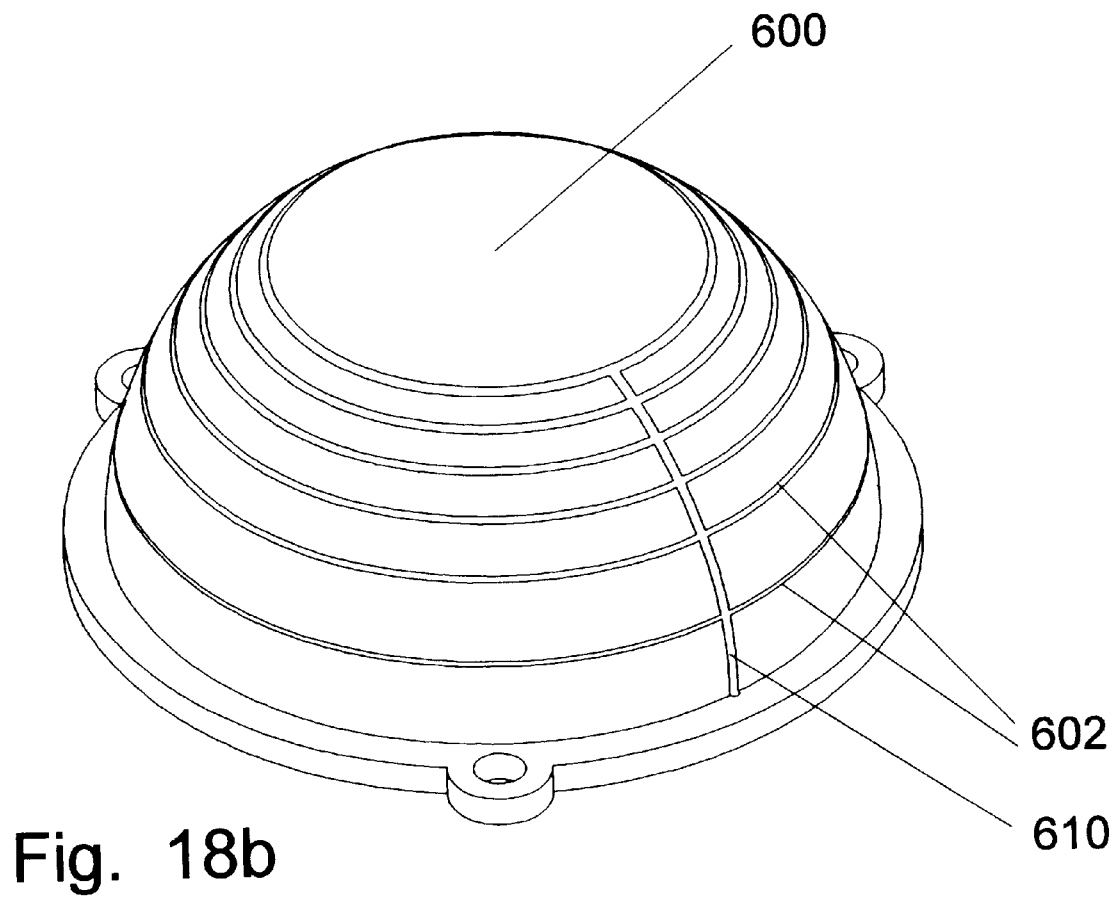
Figure 19:
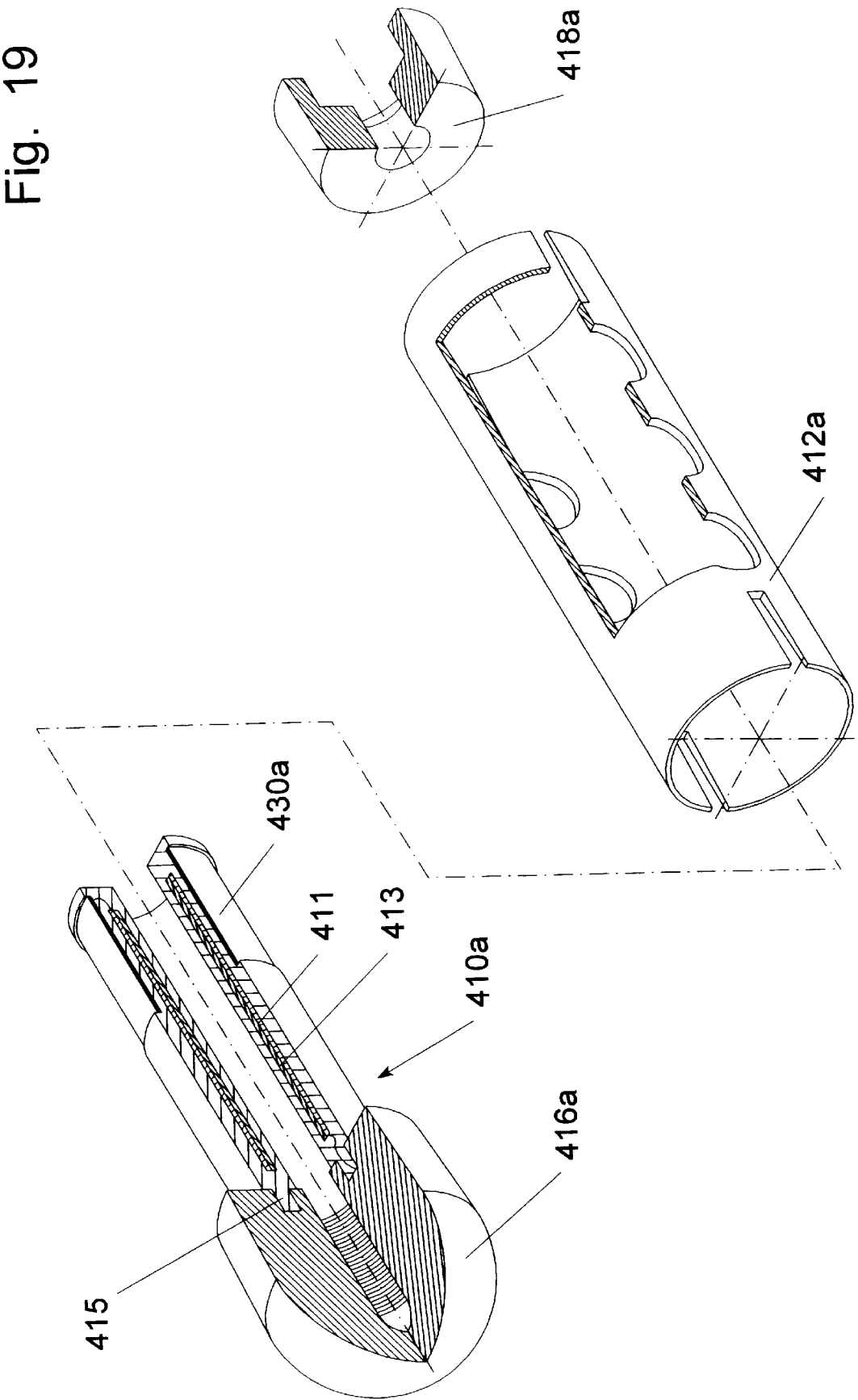

FIGS. 18a and 18b, a sectional and isometric view, respectively, of an hip-joint shell prosthesis; and FIG. 19, an exploded view of an electric dowel according to the invention.

FIG. 1a, on the left and partly in section, shows a femoral head prosthesis 10. This prosthesis has a body in the form of a hollow shaft 12, which on its upper end changes into an integral neck that serves to retain a joint head (not shown). The shaft 12 forms a cavity 16, from which lateral apertures 18 lead to the outside. On the neck end of the cavity 16 is a threaded hole 20, which serves to fill up the shaft and is used for the insertion of an extraction tool; in the known case, it is closed with a drive-in screw 22. The cavity 16 is conventionally filed with spongiosa into which the bone tissue surrounding the implanted shaft is intended to grow. Up to the extent described thus far, this prosthesis 10 is known.

According to the invention, the screw 22 is replaced by an electrifier, which turns the prosthesis into an electric prosthesis in the sense explained at the outset. The device 24 shown on the right in FIG. 1b as an example, whose construction may correspond substantially to that of the device described below in conjunction with FIG. 2, has a head 26 in the form of a hexagon or hexagon socket, a flange, and a thread that fits into the threaded hole 20. The head is adjoined by a rodlike shaft 28, which contains a pickup coil (46 in FIG. 2) that is electrically coupled to two tubular electrodes 30, 32 that surround the shaft, spaced apart longitudinally of the shaft. Located between the electrodes 30, 32 is an electrically insulating portion 34. The shaft 28 is also surrounded by a plurality of insulating annular spacers 36 and it ends in a pointed tip 38 in the form of a mandrel or drill. The electrifier 24 is inserted instead of the screw 22, as indicated by a dot-dashed line 24a, so that the shaft 28 extends into the cavity 16 in the region of the apertures 18. If the prosthesis formed in this way is implanted and the cavity is filled with spongiosa, and if then a low-frequency alternating voltage is induced in the pickup coil by means of an external coil supplied with a low-frequency alternating current, a low-frequency electrical alternating field is created in the interior of the cavity 16, and a low-frequency alternating current flows in the material located in the interior of the cavity 16; as a result, the growth of the bone tissue surrounding the prosthesis shaft 12 into the apertures 18 is promoted, and the hold of the prosthesis is thus secured.

FIG. 2 in longitudinal section shows an electrifier 24a, modified somewhat compared to the electrifier 24 of FIG. 1b, for a prosthesis in accordance with FIG. 1a. The titanium head 26a has a female thread 40 on its lower end, into which an upper end 42 of the shaft 28a, formed as a male thread and having a body 44 of biocompatible plastic, such as PTFE, is screwed. The body 44 encloses a pickup coil 46, whose winding surrounds a magnet core 48, and on the outside the body has two tubular electrodes 30a, 32a, spaced apart longitudinally of the shaft 28a, between which is an insulating strut 50 acting as a spacer. The rounded tip 38a here of the body 44 is thickened and forms a further spacer. The portion of the shaft 28a adjoining the male thread forms a rated breaking point in the form of a constriction 33 or the like, which makes it possible to remove the head 26a and to screw in an extraction tool, without having to remove the shaft 28a of the electrifier, which may have become ingrown, from the prosthesis.

FIG. 3 is a basic illustration of a device according to the invention. The device of FIG. 3 has a body 12b, shown tubular, which forms a cavity 16b and has lateral apertures 18b. One end of the body 12b has an end wall with apertures; an electrifier 24b of the type described in conjunction with FIG. 2 is screwed into the other end. In terms of the function of the device of FIG. 3, the remarks made in conjunction with FIGS. 1a and 1b apply.

FIG. 4a shows an embodiment of the present device that is suitable for instance for permanently implanted tubular osteosynthesis elements or endoprostheses, such as joint prosthesis shafts and intramedullary pins. Such an implant has a tubular body 12c, which encloses a cavity 16c and has lateral apertures 16c. An electrifier 24c, which substantially corresponds to that of FIG. 2 (corresponding parts are identified with the same reference numerals with a "c" appended) is inserted into the cavity 16c. However, it lacks a screw head and is kept spaced apart from the inner wall of the body 12c by annular spacers 36c, which have laterally protruding spring clips 52. The function of the device of FIG. 4a is equivalent to that of FIGS. 1a and 1b.

FIG. 4b shows a brachial joint prosthesis with a tubular shaft 12c into which an electrifier 24c of the kind described in conjunction with FIG. 4a is inserted. Located on one end of the shaft 12c is a joint head 51; the other end has been closed, after the electrifier 24c is inserted, by a plug 53 inserted by press-fitting (or by being screwed in).

FIG. 5 shows a device 24d according to the invention in the form of a tooth implant. It has a tubular jacket or body 12d of tissue-compatible metal, such as titanium, which forms a cavity 16d, has lateral apertures 18d, and is closed at the bottom by a plug 54 press-fitted into it. The other end of the body 16d forms a stable conical prosthesis carrier 55 with a female thread 56. An artificial tooth 58 is secured to the prosthesis carrier 55 with a screw 59 screwed into the female thread. A device 24d of the type shown in FIG. 2 is located in the cavity 16d and has a plastic shaft 44d, which contains a pickup coil 46d with a magnet core 48d and carries electrodes 30d, 32d.

FIG. 6 shows another embodiment of a dental implant. It is equivalent to that of FIG. 5, with the exception that the body 12e forms a thread 60 on the outside, with which the body 16e can be screwed into the jawbone.

FIG. 7a shows a known acetabulum endoprosthesis 70, which according to the invention is provided with an electrifier 24f shown in more detail in FIGS. 7b and 7c. The endoprosthesis 70 is double-walled and forms an annular cavity 16f whose jacket is substantially frustoconical. The outer wall has oblique apertures 18f and protrusions 72 that form a thread so that the prosthesis can be screwed into the hip bone.

The electrifier 24f, as FIGS. 7b and 7c show, takes the form of a flexible band that corresponding to the shape of the cavity 16f is in the form of a circular-annular sector and can be introduced into the cavity 16f through one of the apertures 18f. It contains a striplike magnet core 48f that is surrounded by the winding of a pickup coil 46f. The magnet core and the coil are embedded in a body 44 of a flexible, biocompatible material, such as PTFE. On its side that is toward the apertures in the inserted state, the body carries two striplike electrodes 30f, 32f which are coupled to the ends of the pickup coil 46f, and on the outer edges and between the electrodes 30f, 32f, this body forms three cleatlike spacers 36f.

As FIGS. 8a and 8b show, the pickup coil 46b in the electrifier for the acetabulum prosthesis may also be disposed on one end of a bandlike flexible body 44g, which then acts only as a substrate for the electrodes 30g, 32g, and the spacers 36g. The pickup coil 46g, enveloped with biocompatible material, fits into an oblique aperture 18g. The envelope of the pickup coil 46g is provided with protruding tabs 74 on its ends, so that the enveloped pickup coil 46g can be pressed into the applicable aperture like a plug without dropping into the cavity 16g.

In the modification of the electrifier of FIG. 8b, shown in FIG. 8c, the striplike body 12h now carries only a single electrode 30h and two cleatlike spacers 36h located on either side of the electrode. The second electrode is formed by the metal acetabulum prosthesis, which is electrically contacted via at least one contact piece 76 that is coupled to the second end of the pickup coil 46h. The contact piece 76 is located on one end of the envelope of the pickup coil 46h.

FIGS. 8d and 8e show a further embodiment of an electrifier for a prosthetic acetabulum of the type shown in FIG. 8a. The device 24k has a thin, bandlike substrate 44k, which is shown straight for the sake of simplifying the drawing, rather than curved as in FIGS. 8b and 8c. The substrate 44k has two stamped-out slitlike holes 80 on one end, which form a web 82. A pickup coil 46k is inserted through the holes 80. The substrate 44k also has two rows of paired holes 84 in its longitudinal direction, through which striplike electrodes 30k, 32k are threaded. On one longitudinal edge, the substrate 44k has a plurality of integral tabs 86 with arrowhead-shaped ends 90. The tabs 86 are bent rearward at the dot-dashed lines 92a, 92b, 92c and are inserted by their ends 90 through oblong slots 88. An end piece (closure tab) 93 of the substrate 44k is folded over toward the front on the dot-dashed lines 92d, before the end of the adjacent tab 86 is inserted through the associated oblique slot 88. The spacing between the bending lines 92a and 92b is essentially equivalent to the width of the bandlike substrate 44k. The spacing between the bending lines 92b and 92c is somewhat greater, however, than the width of the substrate 44k, so that the applicable piece 86a (FIG. 8e) of the tab arches upward and acts as a spacer.

FIGS. 9a and 9b show an exemplary embodiment of the present device that serves to promote the buildup of connective tissue and cartilage for a human ear. The device here has a body 12i in the form of a flat bag of meshlike tissue-compatible and optionally resorbable material, which by its nature has apertures (spaces in the mesh) and can be put in a form adapted to the intended use. The meshlike body 12i encloses a space 16i, located in which is a flat, flexible electrifier 24i that contains a flat, flexible pickup coil 46i that has a biocompatible envelope and may be embodied analogously to that of FIGS. 8b and 8c. However, the envelope expediently has electrodes 30i and 32i and spacers 36i on both sides and is adapted in its shape to that of the mesh bag of the implant. If the meshlike body of such a device entirely or partly comprises an electrically conductive material (see German Patent Disclosure DE-A 30 03 758 mentioned at the outset), then the electrodes 30i, 32i on the envelope of the pickup coil 46i may all be connected to one terminal of the pickup coil 46i, while the baglike body 12i is connected as a counter electrode to the other terminal of the pickup coil 46i.

FIG. 10 shows a further embodiment of a dental implant 100 suitable as a carrier for an artificial tooth, not shown. The dental implant has a hollow implantable shaft 102 of an electrically conductive biocompatible material, for instance a metal such as titanium or a cobalt-chromium alloy. The shaft forms a cavity 104, which in its lower portion has a number of windows or apertures 106. On the outside, the shaft is coated with a coating 108 of hydroxyl apatite. The lower end may be rounded or may be provided with a perforated dome-shaped cap 110. On the inside, above the apertures 106, the shaft 102 has an annular shoulder that acts as a seat for an annular disk 112. The annular disk 112 forms a mount for an electrode 114, which has a thinner, lower rodlike part 114a and a thicker upper part 114b, resting on the annular disk, with a female thread 114c. The interstice between the thicker part 114b and the opposed inner wall of the shaft is filled with a solid insulating material 116, such as synthetic resin or cement. To assure a firm connection, the outside of the thicker electrode 114b and the opposed part of the inner wall of the shaft are provided with a thread 118 or are profiled in some other way.

The upper end 102a of the shaft 102 is conical and forms a seat for a separate pickup coil unit 120 mounted on it. This unit has a plastic body 122 that surrounds a multilayer pickup coil 124, located in which is a hollow-cylindrical soft iron magnet core 126. One terminal 124a of the pickup coil 124 is connected to a contact piece 128 whose jacket is frustoconical and which is let into the lower end of the plastic body 122. On its lower end, it has an annular bead 130, which in the mounted state engages an annular groove 131 of the shaft 102 and thereby makes contact with the upper end 102a of the shaft 102. The other terminal 120b of the pickup coil 124 is connected to a funnel-shaped metal sleeve 134 that is let into the other end of the plastic body 122. Extending through the plastic body 122 and the magnet core 126 is an axial conduit 135 that contains an insulating tube 136. On its outside, the plastic body has a male thread 138 onto which an artificial tooth can be screwed.

The artificial tooth, not shown, is fixed on the unit 120 by means of a screw, not shown, analogous to the screw 59 in FIG. 5. The screw extends through the conduit 135 and is screwed into the female thread 114c, so that in addition to the mechanical connection of the artificial tooth, the unit 120 and the shaft 102, it also makes an electrical connection between the terminal 124 and the electrode 114. As in the previous examples, the cavity 104 serves to receive spongiosa and the like.

In general, the body of the present device, if it is entirely or partly made of an electrically conductive material, can act as a second or counterelectrode, which then together with the internal electrode or electrodes forms a kind of coaxial structure and generates a current that flows substantially from the inside outward.

FIG. 11 shows a pickup coil unit 120a similar to the unit 120 of FIG. 10. Here, a threaded sleeve 140 is secured with a connecting bridge 142 onto the male thread of the plastic body 122a.

The implant 100 shown in FIG. 10 may also be used with a spatially separate, independently implantable pickup coil, for instance to reinforce two lumbar vertebrae 150, as shown in FIG. 2. The supply of current to the electrodes of the unit 100 is effected through a spatially remote pickup coil 124x or some other implantable current source, such as an alternating current generator 124y, which is coupled to the shaft 120 or the electrode 114 (FIG. 10) via flexible, insulated lines 152 and a connection cap 154 shown in greater detail in FIG. 13.

The connection cap 154 includes a funnel-shaped contact piece 128a, corresponding to the contact piece 128 of FIG. 10, and a second funnel-shaped contact piece 134b. The contact pieces are separated by an insulator body 122a. The connection cap is connected to the unit 120 by a screw, not shown, in the manner explained for the unit 120 in conjunction with FIG. 10.

FIG. 14a shows a dental implant 200, which includes an implantable first part in the form of a shaft 210 and a second part, which is still accessible from outside once the shaft has been implanted, this part being in the form of an artificial tooth 220. The shaft 210 may correspond in structure to that of FIG. 10; that is, it has a hollow body with an electrically conductive surface and with apertures and with at least one internal electrode. However, the implant 200 contains no pickup coil or other voltage source; instead, the externally accessible second part, or in this case the screwed-on artificial tooth 220, has a connection device, not shown in FIG. 14a, of the type explained in conjunction with FIG. 13, whose power supply leads end in funnel-shaped contact pieces 222, 224, which are let into the surface of the artificial tooth 220 at some cosmetically acceptable point, such as the back side of that tooth.

The power supply to the electrodes (shaft body, internal electrode) of the implant is effective with the aid of a clamp 230, shown in FIG. 14b, which includes a bail 232 of nonconductive material, such as plastic. Secured to the inside of the bail 232 are two conical contact pieces 234, 236, which fit into the contact pieces 222, 224 and can be coupled via flexible lines 238, 240 to a source for a low-frequency alternating voltage, such as a secondary or pickup coil 242 or a function generator 244 or other alternating voltage source. Accordingly here the voltage source is external, is completely separate from the implant, and is connected to the implant only temporarily.

The terminals for the external current source may also be located at other sites, such as on the shaft. The electrodes may also be coupled to an internal pickup coil.

In the device of FIG. 9a as well, instead of the pickup coil 46i—analogously to FIGS. 12, 14a, 14b—a separate, implantable or external alternating voltage source may be used.

FIG. 15 shows a similar device to FIGS. 12 and 13. It includes a perforated cylindrical body of titanium and a closure cap 302 of PTFE. The closure cap retains two axially extending, pinlike electrodes 304, 306 with pointed ends, which are connected to flexible, insulated lines 308, 310 for connecting the electrodes to an implantable pickup coil 342 or some other alternating voltage source 344. If the body 300 is implanted between two vertebrae and filled with spongiosa, the open end of the body is closed with the closure cap 302, and the electrodes penetrate the spongiosa in the body.

FIG. 16a shows the tibia part of the knee-joint prosthesis known from the journal OSTEOLOGIE (loc. cit.). It has a semicircular body 402, on whose underside four cylindrical rings 404 are mounted. The body is secured in the head of the tibia by expanding sleeves or dowels 410 (FIG. 16b) that are passed through the rings 404.

The dowel 410 shown in FIG. 16b includes a perforated cylindrical sleeve 412, which has axial slits on its ends. The ends may be slightly widened conically. The dowel also includes one front and one rear slightly conical end piece 416 and 418, respectively, which can be pressed by means of a screw 420 into the ends of the sleeve 412 and can then spread the slit ends apart.

In the sleeve 412, there is a device 422 for stimulating tissue growth. It is seated on the screw 420, in the mounted state of the dowel 410, and is centered by two annular disks 424. The device 422 includes a pickup coil, which is wound onto a tubular magnet core. The ends of the coil are coupled to annular electrodes 430, 432. Between the electrodes 430, 432 and the inner wall of the sleeve 412, an interstice remains, into which—stimulated by the electrical field or the electrical current between the electrodes—tissue can grow. The dowel 410 may also act as a prosthesis shaft; in that case, the end piece 418 may for instance be embodied as a mount for a femoral head.

Instead of two tubular electrodes, electrodes in the form of halves or quarters and other fractions of a cylinder divided into the longitudinal direction may be used.

FIG. 17a shows a portion of an intramedullary pin 500, which as the cross section of FIG. 17b shows has longitudinal grooves 502, which are narrowed somewhat at their mouth. A device 504 is pressure or thrust into the longitudinal grooves 502. The device 504 includes a wirelike electrode 506, which is surrounded in spaced-apart fashion by a hose 508 that is either perforated or comprises sintered material with large pores. The hose may be of PTFE, and the perforations may be made with a laser. The intramedullary pin 500 and the electrode 506 are connected to a pickup coil (not shown), so that between the electrode and the intramedullary pin 500 an electrical field is created that promotes tissue growth. Once again, tissue can accordingly grow through the slitlike opening of the groove into the space formed by the perforations or pores between the inner wall of the groove of the intramedullary pin and the internal electrode.

Alternatively, two or more devices 504 may be provided in a corresponding number of grooves, and the low-frequency alternating voltage can be applied between the electrodes 506 of these devices 504.

The device 504 may also be used with other implants, such as in the case of a femoral head prosthesis whose shaft is provided with one or more grooves, or an acetabulum prosthesis of the kind shown in FIGS. 18*a* and 18*b*. The acetabulum prosthesis shown there includes a dome-shaped body 600 of titanium or some other tissue-compatible metal. On the outside, the body 600 has a number of annular grooves 602 with slitlike openings that correspond to the grooves 502 in FIG. 17*b*; on the inside, it is lined with a shell 604 of PTFE. A plurality of eyelets 606 are provided on the edge and form holes for securing the prosthesis to the hip bone. The edge includes a groove 608 for a pickup coil, not shown. The grooves 608 communicate via a hole with a meridional groove 610 that intersects the grooves 602.

Devices 504 of the type shown in FIG. 17*c* are introduced into the grooves 602, and their electrodes 506 are connected to the pickup coil via connecting lines that extend in the groove 610. As in FIG. 17*c*, the holes of the insulating hose of the device 504 form cavities that lead from the surface of the electrode to the opening of the groove. The electrodes in the grooves 602 may be connected in alternation to opposite-pole terminals of the pickup coil, or they may all be connected to the one terminal, in which case the body 600 is then connected as a counter electrode. The body may also have one or more spiral grooves, analogous to a single or multiple thread, for corresponding devices 506.

FIG. 19 shows an electric dowel similar to that of FIG. 16*b*. Equivalent elements are therefore identified by the same reference numerals followed by an "a", and the explanation will be limited to the differences.

The device 410*a* of the dowel of FIG. 19 includes only a single tubular electrode 430*a*, which is coupled to a first terminal of a pickup coil 411. The pickup coil 411 is seated on a tubular magnet core 413, and they are both surrounded by the tubular PTFE body of the device 410, which is seated in an annular groove on the rear face end of the end piece 410*a*. The second terminal of the pickup coil is electrically connected via a contacting device 415 to the metal end piece 416*a*, which together with the perforated tubular metal part 412*a* and the likewise metal end piece 418*a* acts as a counter electrode. Otherwise, the dowel of FIG. 19 is equivalent to that of FIG. 16*b*.

We claim:

1. An implantable device with a body (12) suitable for its medical function and comprising biocompatible material, which body forms at least one interior cavity (16) that communicates through at least one opening (18) with the surroundings of the body so that tissue surrounding the implantable device can grow through the at least one opening;

at least two electrodes (30, 32) within said body (12), which electrodes have terminals for supplying a low-frequency electrical alternating voltage and at least one (30) of which is located inside the cavity (16);

characterized in that said at least one electrode (30) is located inside the cavity (16) in such a way that it is surrounded by the inner boundary of the cavity and spaced therefrom to define an interstice between said at least one electrode (30) and the inner boundary of the cavity, into which interstice said tissue can grow from outside inward through the at least one opening (18); and in that a source of said low frequency alternating voltage is provided, electrically coupled to the at least one electrode (30, 32).

2. The device of claim 1, characterized in that at least one second electrode (32) is disposed in the cavity (16).

3. The device of claim 1, characterized by a pickup coil (46) that is electrically coupled to the electrodes (30, 32).

4. The device of claim 1, in which the body has a neck and (12) forms a hollow joint prosthesis shaft that has lateral apertures (18) and has a threaded hole (20) on an end toward the neck, characterized by an electrifier (24) which can be inserted into the threaded hole (20) and has a rodlike shaft (28) extending into the cavity (16), which shaft carries the at least one electrode (30) and contains a pickup coil (46).

5. The device of claim 4, characterized in that the electrifier (24*a*, FIG. 2) contains a screw (26) that fits into the threaded hole (20) and to which the shaft (28*a*) of the electrifier is secured, and that a rated breaking point (33) is provided between the screw and the portion of the shaft adjoining it.

6. The device of claim 1, in which the body takes the form of an acetabulum prosthesis and forms an annular cavity, characterized in that the cavity contains an electrifier (24*f*) with a flexible bandlike body (44*f*) that carries at least one electrode (30*f*) extending circumferentially of the cavity.

7. The device of claim 1, characterized in that the body (12*i*) takes the form of a bag of meshlike material.

8. The device of claim 1, characterized in that the body contains a flat, flexible pickup coil which is provided with an envelope of a biocompatible material on which electrodes (30*i*, 32*i*) and spacers (36*i*) are located (FIGS. 9*a*, *b*).

9. The device of claim 1, which contains an implantable hollow shaft (200) and an artificial tooth (220), characterized in that the artificial tooth (220) has terminals (222) for an external current source, and that the hollow shaft has apertures and contains the at least one electrode, which is coupled to one of the terminals (FIGS. 14*a*, 14*b*).

10. The device of claim 1, characterized in that the body (500, 600) comprising electrically conductive material has at least one groove (502, 602), which has an opening; that an electrode (506) is located in the groove; and that the electrode is surrounded by a perforated, electrically insulating structure (508) that has holes which lead from the electrode to the opening of the groove.

11. The device of claim 2, characterized by a pickup coil (46) that is electrically coupled to the electrodes (30, 32).

12. The device of claim 2, characterized in that the body (12*i*) takes the form of a bag of meshlike material.

13. The device of claim 2, characterized in that the body contains a flat, flexible pickup coil which is provided with an envelope of a biocompatible material on which electrodes (30*i*, 32*i*) and spacers (36*i*) are located (FIGS. 9*a*, *b*).

* * * * *